US012781220B2

(12) United States Patent
Fang et al.

(10) Patent No.: US 12,781,220 B2
(45) Date of Patent: Nov. 3, 2026

(54) CHEMICALLY REVERSIBLE 2'-OH ACYLATION PROTECTS RNA FROM HYDROLYTIC AND ENZYMATIC DEGRADATION

(71) Applicant: The Board of Trustees of the Leland Stanford Junior University, Stanford, CA (US)

(72) Inventors: Linglan Fang, Stanford, CA (US); Eric T. Kool, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 483 days.

(21) Appl. No.: 18/377,236

(22) Filed: Oct. 5, 2023

(65) Prior Publication Data

US 2024/0093184 A1 Mar. 21, 2024

Related U.S. Application Data

(63) Continuation-in-part of application No. PCT/US2023/010686, filed on Jan. 12, 2023.

(60) Provisional application No. 63/299,615, filed on Jan. 14, 2022.

(51) Int. Cl.
*C12N 15/11* (2006.01)
*C07H 21/02* (2006.01)

(52) U.S. Cl.
CPC ............. *C12N 15/11* (2013.01); *C07H 21/02* (2013.01); *C12N 2310/321* (2013.01); *C12N 2310/344* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 3,197,476 | A | 7/1965 | Erner et al. |
| 2004/0116680 | A1 | 6/2004 | Beier at el. |
| 2020/0115372 | A1 | 4/2020 | Petter et al. |

FOREIGN PATENT DOCUMENTS

| | | |
|---|---|---|
| WO | WO 2023137113 | 7/2023 |

OTHER PUBLICATIONS

Velema, Willem A., and Eric T. Kool. "The chemistry and applications of RNA 2'-OH acylation." Nature Reviews Chemistry 4.1 (2020): 22-37.*

Kadina et at. (2018) "RNA Cloaking by Reversible Acylation", Angew Chem tnt Ed Engl. 57(12): pp. 3059-3063.

Li et al. (2020) "Scaffolding-Induced Property Modulation of Chemical Space", ACS Comb. Sci. 22, pp. 356-360.

Flynn et al. (2016) "Transcriptome-wide interrogation of RNA secondary structure in living cells with icSHAPE", Nat Protoc. 11(2): pp. 273-290.

PubChem-CID-68263, Create Date: Mar. 26, 2005 {Mar. 26, 2005), p. 3, figure.

* cited by examiner

*Primary Examiner* — Patrick T Lewis

(74) *Attorney, Agent, or Firm* — Pamela J. Sherwood; Bozicevic, Field & Francis LLP

(57) ABSTRACT

Compositions and methods are provided for the reversible modification of RNA to enhance RNA in-solution and enzymatic stability by reaction with acylimidazoles, sulfonyltriazoles, or sulfonylimidazoles. 2'-OH acylation protects RNA from hydrolytic and enzymatic degradation. Water-soluble organocatalysts can accelerate the reversal of acylation adducts and functionally restore RNAs, alternatively the acylation is spontaneously reversed in a cellular environment. Chemically tuned 2'-OH acylation can be spontaneously released in cells to restore RNA biological functions including translation. mRNA can be selectively modified at the 2'-OH of poly(A)-tail for enhanced in-cell stability and enhanced total protein output.

20 Claims, 14 Drawing Sheets

CHEMICALLY REVERSIBLE 2'-OH ACYLATION PROTECTS RNA FROM HYDROLYTIC AND ENZYMATIC DEGRADATION

CROSS REFERENCE TO OTHER APPLICATIONS

This application claims the benefit of PCT Application No. PCT/US2023/010686, filed Jan. 12, 2023, which claims the benefit of U.S. Provisional Application No. 63/299,615 filed Jan. 14, 2022, the contents of which are hereby incorporated by reference in their entirety.

STATEMENT REGARDING FEDERALLY SPONSORED RESEARCH

This invention was made with Government support under contract GM127295 awarded by the National Institutes of Health. The Government has certain rights in the invention.

BACKGROUND

RNA is useful both as a therapeutic agent, and as an analyte in biological samples. However, it is highly susceptible to degradation from hydrolysis, including in-line hydrolysis and enzyme-mediated reactions. RNA hydrolysis occurs when the deprotonated 2'-OH of the ribose, acting as a nucleophile, attacks the adjacent phosphorus in the phosphodiester bond of the sugar-phosphate backbone of the RNA. The phosphorus then detaches from the oxygen connecting it to the adjacent sugar, resulting in ester cleavage of the RNA backbone. This produces a 2', 3'-cyclic phosphate that can then yield either a 2'- or a 3'-nucleotide when hydrolyzed.

Cleavage is frequently done with catalytic enzymes, which are widely found. For example, Ribonuclease A (RNase A), a protein enzyme contains histidine in its active site, and uses it to accomplish acid-base catalysis and cleavage of RNA. Certain histidine residues in the active site act as bases to remove protons from 2' hydroxyls of ribose sugars, while others act as acids to donate protons to the 5' oxygen of adjacent riboses to make them better leaving groups. A lysine residue, also in the active site of RNase A, stabilizes the negatively charged oxygen atoms in the transition state.

Cleavage can also be enhanced by the presence of small ribonucleolytic ribozymes, such as hammerhead ribozyme, the Hepatitis Delta Virus (HDV) ribozyme, and the hairpin ribozyme. Large ribozymes, such as Group I introns, Group II introns, and RNase P, catalyze splicing and other post-transcriptional modifications during mRNA processing, using the cleavage mechanism described above.

Protection of RNA in samples and therapeutics is of interest, particularly if the protection can be reversed to provide for biologically active RNA molecules. The present disclosure provides such protection and methods for deprotection to restore biologically active RNA molecules.

SUMMARY

Compositions and methods are provided for the protection of RNA from hydrolysis, thereby enhancing RNA in-solution and enzymatic stability. It is demonstrated that selective 2'-hydroxyl acylation of RNA by water-soluble acylimidazole reagents protects RNA from hydrolytic and enzymatic degradation, regardless of the physical-chemical properties of the acyl adducts. Also provided are water soluble organocatalysts that accelerate the reversal of acylation adducts and functionally restore the RNA. It is demonstrated that selected 2'-acylation can be spontaneously reversed in human cells, restoring biologically functional RNA in cells. This RNA preservation platform enhances RNA stability and provides a real-world solution for preserving RNAs, regardless of their origin, during storage and transportation.

Benefits of the methods disclosed herein include, without limitation, the use of water soluble acylimidazole reagents, which allow for 2'-OH acylation in aqueous conditions; and the selectivity of acylimidazole reaction with the 2'-hydroxyl groups of RNA, due to acylimidazoles substantially lacking reactivity with exocyclic amines of the bases. The reversal of acylation in an aqueous buffer at a neutral pH avoids using RNA-damaging, acidic, or basic conditions to reverse acylation. The spontaneous restoration of RNA provides for biological functionality in human cells, including translation of mRNA.

Also provided are bioorthogonal methods for effective reversal of 2'-OH RNA acylation with water soluble organocatalysts that are a strong nucleophile and weak base, performed in aqueous solution at neutral pH, e.g. at a pH from about 7 to about 8, including pH 7.1, 7.2, 7.3, 7.4, 7.5, 7.6, 7.7, 7.8, 7.9, etc. In some embodiments the organocatalyst is Tris (tris(hydroxymethyl)aminomethane). In some embodiments the organocatalyst is DABCO (1,4-diazabicyclo[2.2.2]octane). Buffers for this purpose include, without limitation Tris (tris(hydroxymethyl)aminomethane), etc.

Acylimidazoles useful hi the methods disclosed herein have the general structure:

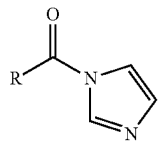

where R is a substituted or unsubstituted alkyl group, a substituted or unsubstituted heteroalkyl group, a substituted or unsubstituted aryl or heteroaryl, a substituted or unsubstituted cycloalkyl. In some embodiments R comprises from 1-10 carbons, and optionally comprises 1-4 heteroatoms, particularly N or O. A suitable acyl group is water-soluble, the ester product of which is relatively water-stable, while being electrophilic enough that allows readily reversal by nucleophilic organocatalysts.

Suitable R groups include, for example:

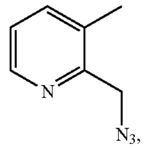 , 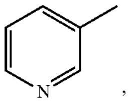 , $CH_3$, 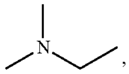 ,

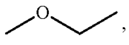 , 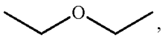 , 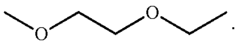 .

Aromatic R groups include:
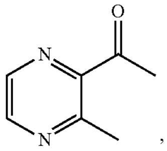, 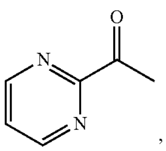, 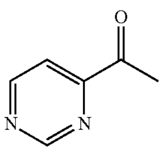,
α-alkoxy adduct R groups include:
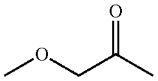, 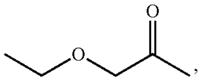,
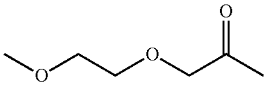, 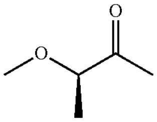,
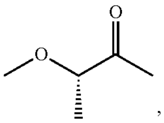, 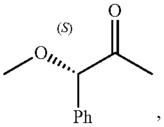, 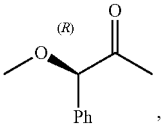,
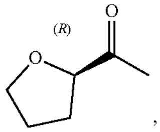, 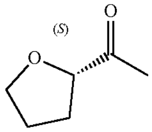
α-phenyl adduct R groups include, for example:
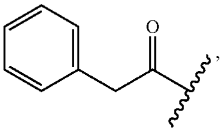, 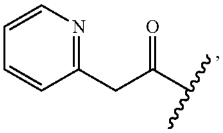,
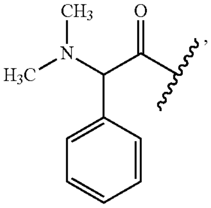, 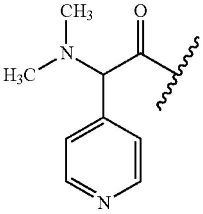,
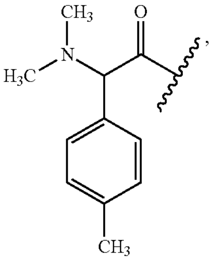, 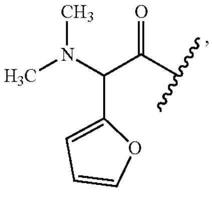,
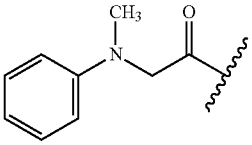 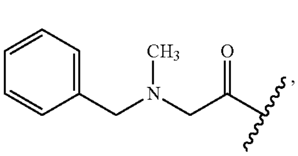,
-continued
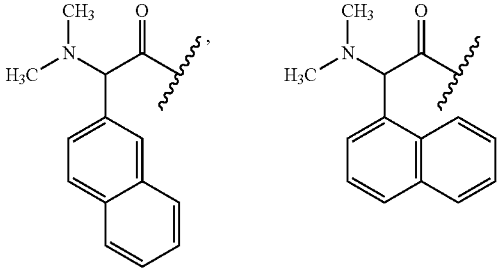,
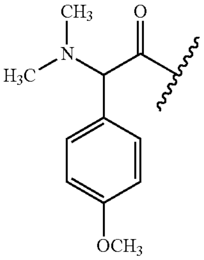.
α-amino adduct R groups include:
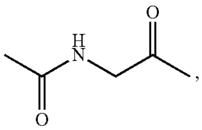, 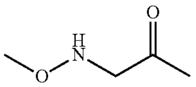,
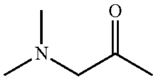, 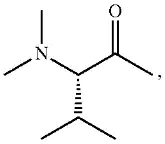, 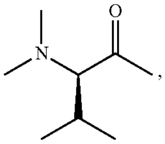,
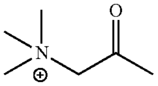, 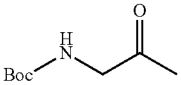,
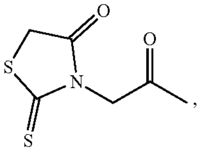, 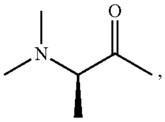, 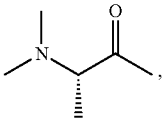,
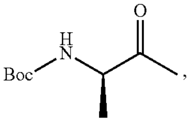, 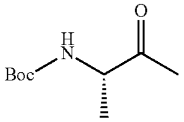,
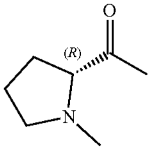, 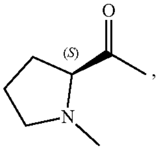, 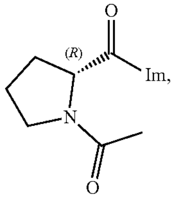,
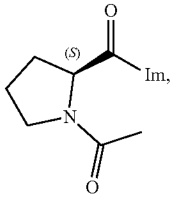, 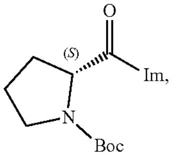, 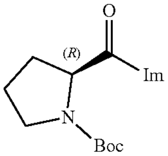

Glutathione-responsive adduct R groups include:

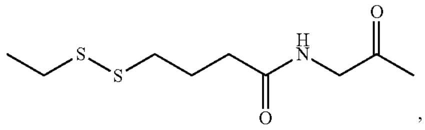
,
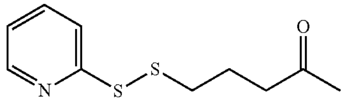

Sultoriylatlon reagents useful in the methods disclosed herein have the general structure:

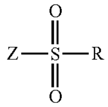

where R is a substituted or unsubstituted alkyl group, a substituted or unsubstituted heteroalkyl group, a substituted or unsubstituted aryl or heteroaryl, a substituted or unsubstituted cycloalkyl; and Z is imidazole, 1,2,3-triazole, or 1,2,4-triazole. In some embodiments R comprises from 1-10 carbons, and optionally comprises 1-4 heteroatoms, particularly N or O. A suitable sulfonyl group is water-soluble, the sulfonylated product of which is relatively water-stable.

Suitable R groups include, for example:

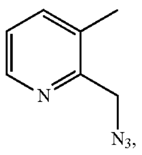
, 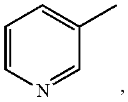
, 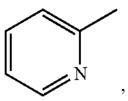
,
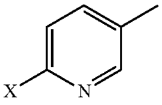
(X = Cl or Br), $CH_3$, 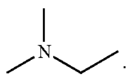
.

The RNA that is protected may be mRNA, tRNA, rRNA, viral RNA, synthetic RNA such as chemically synthesized or in vitro transcribed forms, or any other form of RNA, such as hnRNA and viroid RNA. The RNA may be a mixture of different types of RNA and may be in single- or double-stranded form. The RNA may be synthetic or a natural product. In some embodiments the RNA is an mRNA of eukaryotic or prokaryotic origin. An mRNA may or may not have a cap and/or polyA tail. An RNA may or may not contain unnatural modified nucleobases. An RNA may be at least 12 nt in length, at least about 15, at least about 20, at least about 25, and may be greater than about 100 nt, 500 nt, 750 nt, 1 kb, 1.5 kb, 2 kb, or larger. An RNA can be linear or cyclic. An RNA acylated by the methods disclosed herein may comprise at least about 30% acylated 2'-OH, at least about 50% acylated 2'-OH, at least about 75% acylated 2'-OH, at least about 90% acylated 2'-OH, or more. Upon reversal of acylation, less than about 75% of the RNA may comprise acylated 2'-OH, less than about 50%, less than about 25%. RNA sulfonylated by the methods disclosed herein may comprise at least about 1% sulfonylated 2'-OH, at least about 10% sulfonylated 2'-OH, at least about 20% sulfonylated 2'-OH, at least about 30% sulfonylated 2'-OH, or more.

Also provided are biorthogonal methods for selective post-synthetic modification, of 2'-OH groups within the poly(A)-tail of mRNA, In some such embodiments, the modification is selectively performed on the poly-A tail. The selective modification of the poly-A tail can enhance translation of the mRNA in an in vitro translation system or a cell, e.g. increasing by at least 2-fold, at least 5-fold, at least 8-fold, at least 10-fold or more. The reaction may be performed with acylimidazole reagents or sulfonylation reagents, performing in aqueous solution at neutral pH, e.g. at a pH from about 7 to about 8, including pH 7.1, 7.2, 7.3, 7.4, 7.5, 7.6, 7.7, 7.8, 7.9, etc. Reversal of 2'-OH RNA acylation may be omitted for this embodiment.

In some embodiments, modification of the poly-A tail is performed with an acylimidazole reagent, e.g. as disclosed herein. In some embodiments the reactant comprises an aryl R group, e.g. an α-phenyl substituted acylimidazole. The reactant may be a racemic mixture, or may be a substantially pure stereoisomer. In some embodiments the acyl group is N,N-dimethyl-phenylglycine. In some embodiments the acyl group is N,N-dimethyl-phenylglycine (R enantiomer).

Selective modification of the poly-A tail can be achieved by hybridizing the mRNA to complementary DNA specific for sequences other than the poly-A tail, for example the 5'-UTR, open reading frame, and 3'-UTR of the mRNA, which blocks acylation of the hybridized regions. In some embodiments the 5'-UTR, open reading frame, 3'-UTR of mRNA are hybridized with complementary DNA oligos, with a length ranging from about 18 nt to about 120 nt. In some embodiments, substantially the entire mRNA sequence, apart from the poly-A tail is hybridized. In alternative embodiments a single strand of complementary DNA that hybridizes to the 5'-UTR, open reading frame, and 3'-UTR of the mRNA, e.g. synthesized by reverse transcriptase. Subsequent removal of the DNA strand with DNases produces mRNA with 2'-modifications at its poly (A)-tail.

Where the acylation is selectively present on the poly-A tail, the region of the poly-A tail may comprise at least about 10%, at least about 20%, at least about 30%, at least about 50% acylated, at least about 75%, at least about 90% acylated 2'-OH, or more. The enhancement of translation may increase with the level of acylation.

In some embodiments a method is provided for reversable protection of RNA, the method comprising contacting, in aqueous solution, RNA with an acylimidazole. Acylimidazoles may be present in the aqueous solution at a concentration of from about 1 mM, about 50 mM, about 100 mM, about 150 mM, about 200 mM, about 400 mM, and not more than about 600 mM. The reaction is performed at a temperature from 4° C. to about 3TC, and may be from about 10° to about 25° , for example at room temperature, for a period of from about 1 minute to about 4 hours. Reacting the RNA with the acylimidazole solution produces modified RNA comprising acylated 2'-OH ribose. Optionally, after a desired period of time, the acylation is reversed with a water soluble organocatalyst that is a strong nucleophile and weak base, performed in aqueous solution at neutral pH. Further provided are methods for protection of RNA, including RNA in solution, during manipulation, shipping, in cultured human cells, etc., by reversible acylation.

Modification at the 2'-OH position is preferably substantially regiospecific. Thus, there is preferably substantially no modification of the bases, phosphodiester bonds and/or any other position within the RNA chain other than the 5'-OH and 3'-OH groups. In this way, the polynucleotide retains important properties of the RNA.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION

Figure 1:
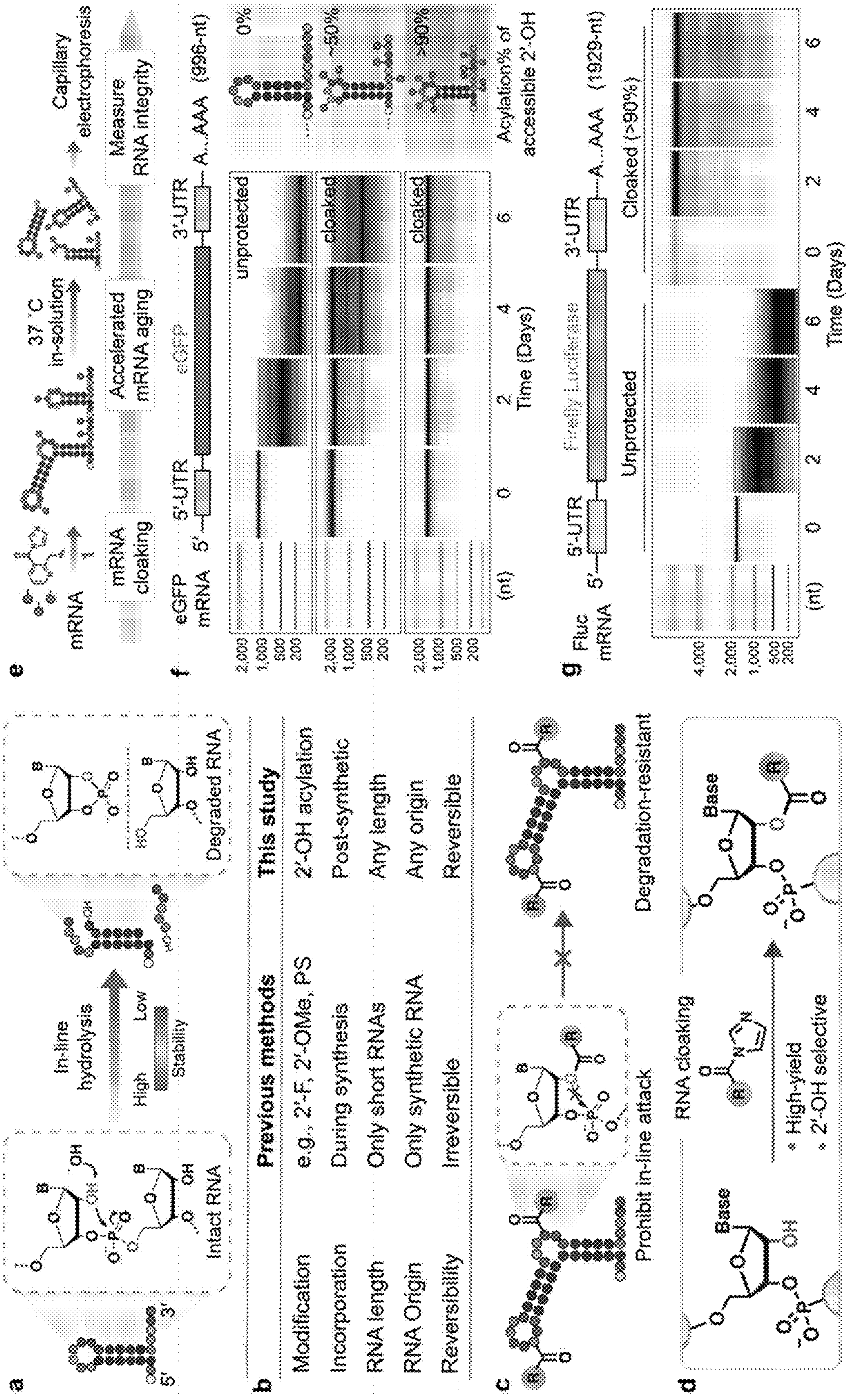
FIG. 1. RNA 2'-OH acylation inhibits thermal degradation of RNA.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms “a”, “an”, and “the” include plural referents unless the context clearly dictates otherwise. Thus, for example, reference to “a cell” includes a plurality of such cells and reference to “the peptide” includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As used herein, compounds which are “commercially available” may be obtained from commercial sources including but not limited to Acros Organics (Pittsburgh PA), Aldrich Chemical (Milwaukee WI, including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester PA), Crescent Chemical Co. (Hauppauge NY), Eastman Organic Chemicals, Eastman Kodak Company (Rochester NY), Fisher Scientific Co. (Pittsburgh PA), Fisons Chemicals (Leicestershire UK), Frontier Scientific (Logan UT), ICN Biomedicals, Inc. (Costa Mesa CA), Key Organics (Cornwall U.K.), Lancaster Synthesis (Windham NH), Maybridge Chemical Co. Ltd. (Cornwall U.K.), Parish Chemical Co. (Orem UT), Pfaltz & Bauer, Inc. (Waterbury CN), Polyorganix (Houston TX), Pierce Chemical Co. (Rockford IL), Riedel de Haen AG (Hannover, Germany), Spectrum Quality Product, Inc. (New Brunswick, NJ), TCI America (Portland OR), Trans World Chemicals, Inc. (Rockville MD), Wako Chemicals USA, Inc. (Richmond VA), Novabiochem and Argonaut Technology.

As used herein, “methods known to one of ordinary skill in the art” may be identified through various reference books and databases. Suitable reference books and treatises that detail the synthesis of reactants useful in the preparation of compounds of the present invention, or provide references to articles that describe the preparation, include for example, “Synthetic Organic Chemistry”, John Wiley & Sons, Inc., New York; S. R. Sandler et al., “Organic Functional Group Preparations,” 2nd Ed., Academic Press, New York, 1983; H. O. House, “Modern Synthetic Reactions”, 2nd Ed., W. A. Benjamin, Inc. Menlo Park, Calif. 1972; T. L. Gilchrist, “Heterocyclic Chemistry”, 2nd Ed., John Wiley & Sons, New York, 1992; J. March, “Advanced Organic Chemistry: Reactions, Mechanisms and Structure”, 4th Ed., Wiley- Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services.

The term "Alkyl" refers to a $C_1$-$C_{20}$ alkyl that may be linear, branched, or cyclic. "Lower alkyl", as in "lower alkyl", or "substituted lower alkyl", means a $C_1$-$C_{10}$ alkyl. The term "alkyl", "lower alkyl" or "cycloalkyl" includes methyl, ethyl, isopropyl, propyl, butyl, isobutyl, sec-butyl, tert-butyl, pentyl, neopentyl, hexyl, cyclopropyl, cyclopropylmethyl, cyclobutyl, cyclobutylmethyl, cyclopentyl, cyclopentylmethyl, cyclohexyl, cyclohexylmethyl, $C_6$ to $C_{12}$ spirocycles, cyclopropylethyl, cyclobutylethyl, decalinyl, Bicyclo-[1.1.1]-pentyl, norboranyl, bicylo-[2.2.2]-octyl, cubyl, adamantanyl and related cage hydrocarbon moieties. In certain embodiments, the alkyl is a $C_1$-$C_{20}$ alkyl. In certain embodiments the alkyl group is poly deuterated.

A "substituted alkyl" is an alkyl which is typically mono-, di-, or tri-substituted with heterocycloalkyl, aryl, substituted aryl, heteroaryl, nitro, cyano (also referred to herein as nitrile), azido, halo, —OR, —SR, —$SF_5$, —CHO, —COR, —C(O)OR, —C(O)—N—$R_2$, —OC(O)R, —OC(O)$NR_2$, —OC(O)OR, —P(O)$(OR)_2$, —OP(O)$(OR)_2$, —$NR_2$, —$N^+R_3$ (wherein a counterion may be present), —$CONR_2$, —NRCOR, —NHC(O)OR, —NHC(O)$NR_2$, —NHC(NH)$NR_2$, $SO_3$, —$SO_2$OR, —$OSO_2$R, —$SO_2NR_2$, or —$NRSO_2$R, where each R is, independently, hydrogen, lower alkyl, R'-substituted lower alkyl, aryl, R'-substituted aryl, heteroaryl, heteroaryl(alkyl), R'-substituted aryl(alkyl), or aryl(alkyl) and each R' is, independently, hydroxy, halo, alkyloxy, cyano, thio, $SF_5$, nitro, alkyl, halo- alkyl, or amino. Substituted alkyls which are substituted with one to three of the substituents selected from the group consisting of alkynyl, cyano, halo, alkyloxy, thio, nitro, amino, or hydroxy are particularly of interest.

The term "Aryl" refers to an aromatic ring having (4n+2) pi electrons that may contain 6 to 20 ring carbon atoms, and be composed of a single ring (e.g., phenyl), or two or more condensed rings, such as 2 to 3 condensed rings (e.g., naphthyl), or two or more aromatic rings, such as 2 to 3 aromatic rings, which are linked by a single bond (e.g., biphenylyl). In certain cases, the aryl is $C_6$-$C_{16}$ or $C_6$ to $C_{14}$. In certain embodiments the alkyl group has one or more hydrogen atoms replaced with deuterium.

Heteroaryl means an aromatic ring system containing (4n+2)pi electrons and comprised of 1 to 10 ring carbon atoms and 1 to 5 heteroatoms selected from O, N, S, Se, having a single ring (e.g., thiophene, pyridine, pyrazine, imidazole, oxazole, tetrazole, etc.), or two or more condensed rings, for example 2 to 3 condensed rings (e.g., indole, benzimidazole, quinolone, quinoxaline, phenothiazine, etc.), or two or more aromatic rings, such as 2 to 3 aromatic rings, which are linked by a single bond (e.g., bipyridyl). In some cases, the heteroaryl is $C_1$-$C_{16}$, and a selection of 1 to 5 heteroatoms consisting of S, Se, N, and O.

The term "heterocycloalkyl", "heterocycle", "heterocyclic group" or "heterocyclyl" refers to a saturated or unsaturated nonaromatic ring system containing 1 to 10 ring carbon atoms and 1 to 5 heteroatoms selected from O, N, S, Se, having a single ring (e.g., tetrahydrofuran, aziridine, azetidine, pyrrolidine, piperidine, tetrathiopyran, hexamethylene oxide, oxazepane, etc.), or two or more condensed rings, such as 2 to 3 condensed rings (e.g., indoline, tetrahydrobenzodiazapines, etc., including fused, bridged and spiro ring systems, having 3-15 ring atoms, included 1 to 4 heteroatoms. In certain cases, the heterocycloalky is $C_1$-$C_{16}$, and a selection of 1 to 5 heteroatoms consisting of S, Se, N, and O. In fused ring systems, one or more of the rings can be cycloalkyl, heterocycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —$SO_2$— moieties.

Examples of heterocycles and heteroaryls include, but are not limited to, azetidine, pyrrole, imidazole, benzimidazole, pyrazole, benzopyrazole, tetrazole, 1,2,3-triazole, benzotriazole, 1,2,4-triazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, benzoisothiazole, phenazine, isoxazole, benzoisooxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, benzothiazole, thiazolidine, furan, benzofuran, thiophene, benzothiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, benzotetrahydrofuranyl, and the like.

Substituted heterocycloalkyl, aryl, heteroaryl are optionally substituted with, hydrogen, 1 to 3 alkyl, alkenyl, alkynyl, cycloalkyl, cycloalkyl(alkyl), aryl, substituted aryl, aryl (alkyl), —$SO_2NR^5R^5$, —$PO_3H_2$, —$NR^5SO_2R^6$ or —$NR^5C(=O)R^6$, wherein $R^5$ and $R^6$ are independently, hydrogen, alkyl, alkenyl, alkynyl, cycloalkyl, cycloalkyl(alkyl), aryl, optionally substituted heterocycloalkyl, aryloxy, heteroaryl, heteroaryl(alkyl), or $R^5$ and $R^6$ together are —$(CH_2)_{3-6}$- or —$(CH_2)_{0-3}X(CH_2)_{0-3}$- where X=NR, O, S, $SO_2$, substituted aryl(alkyl), halo(alkyl), $SF_5$, $NR^5{}_3{}^+$, azido, cyano (also referred to herein as nitrile), —$OR^5$, —$SR^5$, —$NR^5R^6$, halogen, nitro, $SCH_3$, $OCF_3$, $SO_2CH_3$, $SCF_3$, $SO_2CF_3$, $CF_3$, —$SO_2Or^5$, —$OSO_2R^5$, $CCl_3$, —C(=O)$^5$, —C(=O)$OR^5$; —C(=O)$NR^5R^6$, —OC(=O)$R^5$.

By "substituted" as in "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

The term "water-soluble group" refers to a functional group that is well solvated in aqueous environments and that imparts improved water solubility to the compound to which it is attached. Water-soluble groups of interest include, but are not limited to, polyalcohols, straight chain or cyclic saccharides, primary, secondary, tertiary, or quaternary amines and polyamines, sulfate groups, sulfonate groups, sulfinate groups, carboxylate groups, phosphate groups, phosphonate groups, phosphinate groups, ascorbate groups, glycols, including polyethylene glycols (PEG) and modified PEGs, and polyethers. In some instances, water-soluble groups are primary, secondary, tertiary, and quaternary amines, carboxylates, phosphonates, phosphates, sulfonates, sulfates, $—N(H)_{0-1}(CH_2CH_2OH)_{1-2}$, $—NHCH_2CH_2N(CH_3)_{2-3}$, $—NHCH_2CH_2SO_3H$, $—NHCH_2CH_2PO_3H_2$ and $—NHCH_2CH_2CO_2H$, $—(CH_2CH_2O)_{yy}CH_2CH_2XR^{yy}$, $—(CH_2CH_2O)_{yy}CH_2CH_2X—$, $—X(CH_2CH_2O)_{yy}CH_2CH_2—$, glycol, oligoethylene glycol, and polyethylene glycol, wherein yy is selected from 1 to 1000, X is selected from O, S, and $NR^{ZZ}$, and $R^{ZZ}$ and $R^{YY}$ are independently selected from H and C1-3 alkyl.

The term "carboxy isostere" refers to standard medicinal bioisosteric replacement groups for carboxylic acids, amides and ester. These include, but are not limited to: acyl cyanamide, tetrazoles, hydroxychromes, 3-hydroxy-1,2,4-triazoles, 1-hydroxy pyrazoles, 2,4-dihydroxy imidazoles, 1-hydroxy imidazole, 1-hydroxy 1,2,3-triazole, alkylsulfonyl carboxamides, hydroxy isoxazoles, 5-hydroxy 1 ,2,4-oxadiazoles, thiazoles, 1,2,4-oxadiazoles, 1,2,4-oxadiazolones, oxazoles, triazoles, thiazoles, others hydroxamic acids, sulfonimide, acylsulfonamide, sulfonylureas, oxadiazolone, thiazolidinediones, oxadiazole, thiadiazole, isothiazoles, difluorophenols, tetramic acids, tetronic acids, squaric acids, hydroxyquinoline-ones, hydroxyquinoline-2-ones, boronic acids and phosphoric acids.

As used herein the term "PEG" refers to a polyethylene glycol or a modified polyethylene glycol. Modified polyethylene glycol polymers include a methoxypolyethylene glycol, and polymers that are unsubstituted or substituted at one end with an alkyl, a substituted alkyl or a substituent (e.g., as described herein).

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)-X where X is halo), C2-C24 alkylcarbonato (—O(CO)—O-alkyl), C6-C20 arylcarbonato (—O—(CO)—O-aryl), carboxy (—COOH), carboxylato (—COO—), carbamoyl ($—(CO)—NH_2$), mono-substituted $C_1$-$C_{24}$ alkylcarbamoyl (—(CO)—NH(C1-C24 alkyl)), di-substituted alkylcarbamoyl ($—(CO)—N(C1\text{-}C24\ alkyl)_2$), mono-substituted arylcarbamoyl (—(CO)—NH-aryl), thiocarbamoyl ($—(CS)—NH_2$), carbamido ($—NH—(CO)—NH_2$), cyano (—C≡N), isocyano (—N+≡C—), cyanato (—O—C≡N), isocyanato (—O—N+≡C—), isothiocyanato (—S—C≡N), azido (—N═N+═N—), formyl (—(CO)—H), thioformyl (—(CS)—H), amino ($—NH_2$), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR═NH where R=hydrogen, C1 -C24 alkyl, C5-C20 aryl, C6-C20 alkaryl, C6-C20 aralkyl, etc.), alkylimino (—CR═N(alkyl), where R=hydrogen, alkyl, aryl, alkaryl, etc.), arylimino (—CR═N(aryl), where R=hydrogen, alkyl, aryl, alkaryl, etc.), nitro ($—NO_2$), nitroso (—NO), sulfo ($—SO_2—OH$), sulfonato ($—SO_2—O—$), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl ($—SO_2$-alkyl), C5-C20 arylsulfonyl ($—SO_2$-aryl), phosphono ($—P(O)(OH)_2$), phosphonato ($—P(O)(O—)_2$), phosphinato ('P(O)(O—)), phospho ($—PO_2$), and phosphino ($—PH_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with $═O$, $═NR^{70}$, $═N—OR^{70}$, $═N_2$ or $═S$) on saturated carbon atoms in the specified group or radical are, unless otherwise specified, $—R^{60}$, halo, $═O$, $—OR^{70}$, $—SR^{70}$, $—NR^{80}R^{80}$, trihalomethyl, —CN, —OCN, —SCN, —NO, $—NO_2$, $═N_2$, $—N_3$, $—SO_2R^{70}—SO_2O^-M^+$, $—SO_2OR^{70}$, $—OSO_2R^{70}$, $OSO_2O^-M^+$, $OSO_2OR^{70}$, $—P(O)(O^-)_2(M^+)_2$, $—P(O)(OR^{70})O^-M^+$, $—P(O)(OR^{70})_2$, $—C(O)R^{70}$, $—C(S)R^{70}$, $—C(N^{70})R^{70}$, $—C(O)O^-M^+$, $—C(O)OR^{70}$, $—C(S)OR^{70}$, $—C(O)NR^{80}R^{80}$, $—C(NR^{70})NR^{80}R^{80}$, $—OC(O)R^{70}$, $—OC(S)R^{70}$, $—OC(O)O^-M^+$, $—OC(O)OR^{70}$, $—OC(S)O^{70}$, $—NR^{70}C(O)^{70}$, $—NR^{70}C(S)R^{70}$, $—NR^{70}CO_2^-M^+$, $—NR^{70}CO_2R^{70}$, $—NR^{70}C(S)OR^{70}$, $—NR^{70}C(O)NR^{80}R^{80}$, $—NR^{70}C(NR^{70})R^{70}$ and $—NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, $—NR^{80}R^{80}$ is meant to include —$NH_2$, —NH-alkyl, N-pyrrolidinyl, N-piperazinyl, 4N-methyl-piperazin-1-yl, N-morpholinyl, —$N(H)_{0-1}(CH_2CH_2OH)_{1-2}$, —$NHCH_2CH_2N(CH_3)_{2-3}$, —$NHCH_2CH_2SO_3H$, —$NHCH_2CH_2P_3H_2$ and —$NHCH_2CH_2CO_2H$.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$NO_2$, —$N_3$, —$SO_2R^{70}$—$SO_3^-$ $M^+$, —$SO_2OR^{70}$, —$OSO_2R^{70}$, $OSO_2O^-M^+$, $OSO_3OR^{70}$, —$PO_3^{-2}(^+)_2$, —$P(O)(OR^{70})O^-M^+$, —$P(O)(OR^{70})_2$, —$C(O)R^{70}$, —$C(S)R^{70}$, —$C(N^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, $(O)O^-M^+$, —$OCO_2R^{70}$, —$OC(S)O^{70}$, —$NR^{70}C(O)^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, and M+are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, $OS(O)_2R^{70}$, —$OS(O)_2O^-M^+$, —$SO_2OR^{70}$, —$OSO_2R^{70}$, $OSO_2O^-M^+$, $OS(O)_2OR^{70}$, —$P(O)(O^-)_2(M^+)_2$, —$P(O)(OR^{70})O^-M^+$, —$P(O)(OR^{70})(OR^{70}$, —$C(O)R^{70}$, —$C(S)R^{70}$, —$C(N^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

Salts include but are not limited to: Na, K, Ca, Mg, ammonium, tetraalkyl ammonium, aryl and alkyl sulfonates, phosphates, carboxylates, sulfates, Cl, Br, and guanidinium.

Unless otherwise specified, reference to an atom is meant to include isotopes of that atom. For example, reference to H is meant to include $^1H$, $^2H$ (i.e., D) and $^3H$ (i.e., T), and reference to C is meant to include $^{12}C$ and all isotopes of carbon (such as $^{13}C$).

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "heterocycloalkyl(alkyl)" refers to the group (heterocycloalkyl)-(alkyl)-.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound, e.g. an (R) or (S) isomer of an acyl group. Salts, solvates, hydrates, and prodrug forms of a compound are also of interest. Polymorphic, pseudo-polymorphic, amorphous and co-crystal forms of a compound are also of interest. All such forms are embraced by the present disclosure. Thus, the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The term "sample" with reference to a patient encompasses blood and other liquid samples of biological origin, solid tissue samples such as a biopsy specimen or tissue cultures or cells derived therefrom and the progeny thereof. The term also encompasses samples that have been manipulated in any way after their procurement, such as by treatment with reagents; washed; or enrichment for certain cell populations, such as diseased cells. The definition also includes samples that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's diseased cell, e.g., a sample comprising polynucleotides and/or polypeptides that is obtained from a patient's diseased cell (e.g., a cell lysate or other cell extract comprising polynucleotides and/or polypeptides); and a sample comprising diseased cells from a patient. A biological sample comprising a diseased cell from a patient can also include non-diseased cells.

Methods

In some embodiments a method is provided for reversable protection of RNA, the method comprising (i) contacting, in aqueous solution, RNA with an acylimidazole; (ii) reacting the RNA with the reaction system to produce modified RNA comprising acylated 2'-OH ribose; and (iii) optionally after a desired period of time, reversing the acylation with a water soluble organocatalyst that is a strong nucleophile and weak base, performed in aqueous solution at neutral pH; or (iv) optionally after a desired period of time, reversing the acylation spontaneously in cells after transfected into cells with transfection reagents.

Acylimidazoles useful in the methods disclosed herein have the general structure:

I

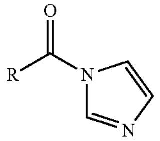

where R is a substituted or unsubstituted alkyl group, a substituted or unsubstituted heteroalkyl group, a substituted or unsubstituted aryl or heteroaryl, a substituted or unsubstituted cycloalkyl. In some embodiments R comprises from 1-10 carbons, and optionally comprises 1-4 heteroatoms, particularly N or O.

R groups may include, for example:

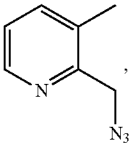, 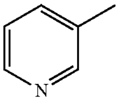, $CH_3$, 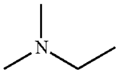,

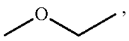, 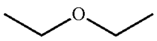, 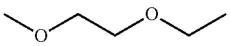.

Aromatic R groups include:

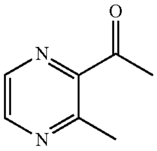, 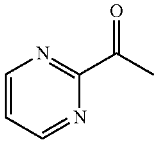, 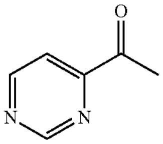

α-alkoxy adduct R groups include:

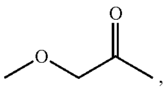, 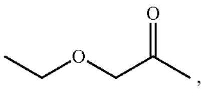,

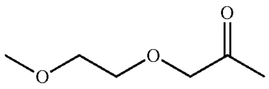, 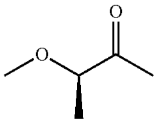,

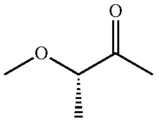, 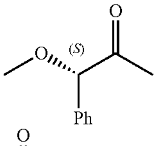,

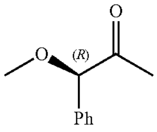, 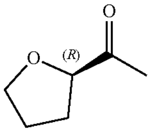, 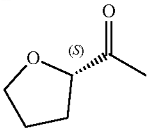

α-phenyl adduct R groups include:

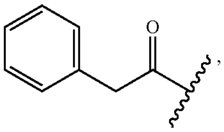, 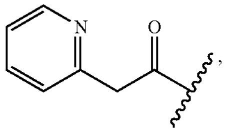,

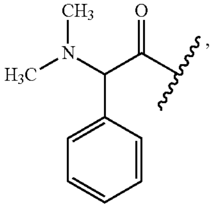, 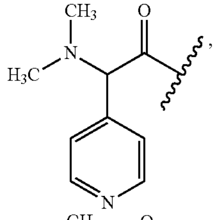,

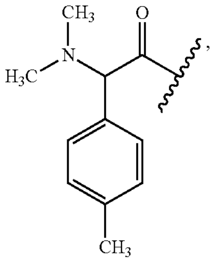, 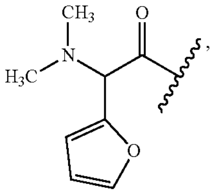,

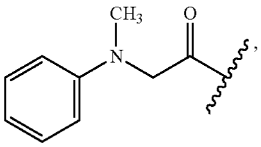,

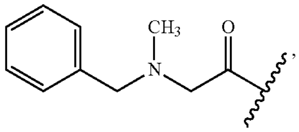,

-continued

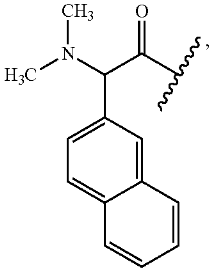,

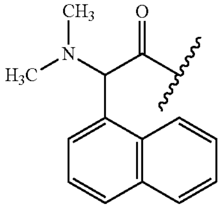,

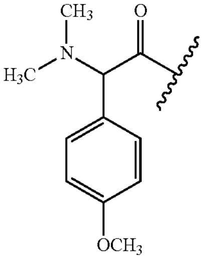

α-amino adduct R groups include:

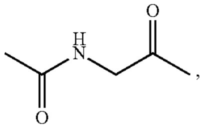,

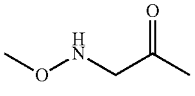,

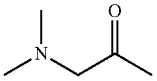,

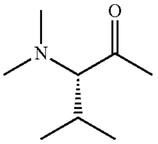,

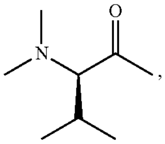,

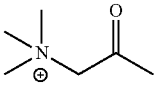,

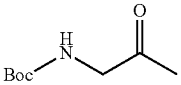,

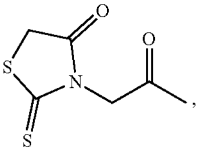,

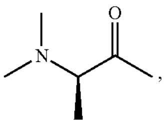,

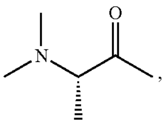,

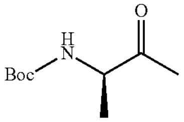,

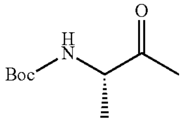,

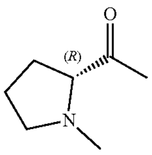,

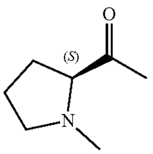,

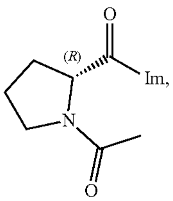,

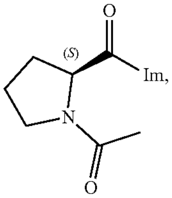,

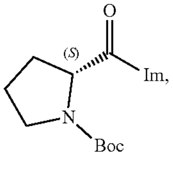,

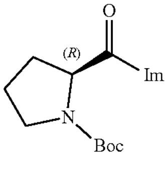

Glutathione-responsive adduct R groups include:

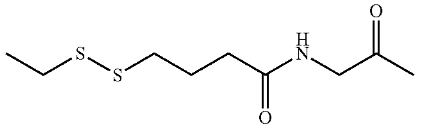,

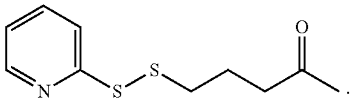.

Sulfonyiation reagents useful in the methods disclosed herein have the general structure:

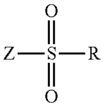

where R is a substituted or unsubstituted alkyl group, a substituted or unsubstituted heteroalkyl group, a substituted or unsubstituted aryl or heteroaryl, a substituted or unsubstituted cycloalkyl; and Z is imidazole, 1,2,3-triazole, or 1,2,4-triazole. In some embodiments R comprises from 1-10 carbons, and optionally comprises 1-4 heteroatoms, particularly N or O. A suitable sulfonyl group is water-soluble, the sulfonylated product of which is relatively water-stable.

Suitable R groups include, for example:

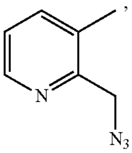,

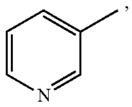,

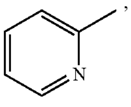,

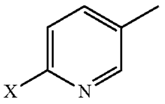

(X = Cl or Br), $CH_3$,

Provided are biorthogonal methods for selective post-synthetic modification of 2'-OH groups within the poly(A)-tail of mRNA with acylimidazole reagents and sulfonylation reagents, performing in aqueous solution at neutral pH, e.g. at a pH from about 7 to about 8, including pH 7.1, 7.2, 7.3, 7.4, 7.5, 7.6, 7.7, 7.8, 7.9, etc. In some embodiments the 5'-UTR, open reading frame, 3'-UTR of mRNA is hybridized with complementary DNA oligos, with a length ranged from about 18 nt to about 120 nt. The poly(A)-tail of the mRNA-DNA hybrids are selectively modified with acylidazoles, sulfonyltriazoles, or sulfonylimidazoles, etc. Subsequent removal of complementary DNA oligos with DNases produces mRNA with 2'-modifications at its poly(A)-tail.

The RNA for protection may be mRNA, tRNA, rRNA, viral RNA, synthetic RNA such as chemically synthesized or in vitro transcribed forms, or any other form of RNA, such as hnRNA and viroid RNA. The RNA may be a mixture of different types of RNA and may be in single- or double-stranded form. The RNA may be synthetic or a natural product. In some embodiments the RNA is an mRNA of eukaryotic or prokaryotic origin. An mRNA may or may not have a cap and/or polyA tail. An RNA may be at least 12 nt in length, at least about 15, at least about 20, at least about 25, and may be greater than about 100 nt, 500 nt, 750 nt, 1 kb, 1.5 kb, 2 kb, or larger. An RNA can be linear or cyclic. An RNA may contain modified unnatural nucleobases. An RNA acylated by the methods disclosed herein may comprise at least about 30% acylated 2'-OH, at least about 50% acylated 2'-OH, at least about 75% acylated 2'-OH, at least about 90% acylated 2'-OH, or more.

Bioorthogonal methods are provided for effective reversal of 2'-OH RNA acylation with water-soluble organocatalysts that are a strong nucleophile and weak base, performed in aqueous solution at neutral pH, e.g. at a pH from about 7 to about 8, including pH 7.1, 7.2, 7.3, 7.4, 7.5, 7.6, 7.7, 7.8, 7.9, etc. In some embodiments the organocatalyst is Tris (tris (hydroxymethyl)aminomethane). In some embodiments the organocatalyst is DABCO (1,4-diazabicyclo[2.2.2]octane).

Buffers for reversal of acylation include, without limitation Tris (tris(hydroxymethyl)aminomethane), DABCO (1,4-diazabicyclo[2.2.2]octane), NaCN, etc. Buffers may be present at a concentration of from about 1 mM, about 5 mM, about 10 mM, about 25 mM, about 50 mM, about 100 mM, and not more than about 250 mM. The reaction is performed at a temperature from room temperature to 37° C., for a period of from about 1 minute to about 24 hours, from about 30 minutes to about 12 hours.

Upon reversal of acylation, less than about 75% of the RNA may comprise acylated 2'-OH, less than about 50%, less than about 25%. The de-acylated RNA is biologically active, and can be used in hybridization, translation, reverse transcription, Cas9-mediated gene editing, etc. reactions.

Also provided are biorthogonal methods for selective post-synthetic modification of 2'-OH groups within the poly(A)-tail of mRNA. In some such embodiments, the modification is selectively performed on the poly-A tail. The selective modification of the poly-A tail can enhance translation of the mRNA in an in vitro translation system or a cell, e.g. increasing by at least 2-fold, at least 3-fold, at least 4-fold, at least 5-fold, at least 6-fold, at least 7-fold, at least 8-fold or more.

In some embodiments, modification of the poly-A tail is performed with an acylimidazole reagent, which may comprise an aryl R group, e.g. an α-phenyl substituted imidazole. The reactant may be a racemic mixture, or may be a substantially pure enantiomer. In some embodiments the acyl group is N,N-dimethyl-phenylglycine. In some embodiments the acyl group is N,N-dimethyl-phenylglycine (R enantiomer).

Selective modification of the poly-A tail can be achieved by hybridizing the 5'-UTR, open reading frame, and 3'-UTR of the mRNA to complementary DNA, which blocks acylation of the hybridized regions. In some embodiments the 5'-UTR, open reading frame, 3'-UTR of mRNA are hybridized with complementary DNA oligos, with a length ranging from about 18 nt to about 120 nt. In some embodiments, substantially the entire mRNA sequence, apart from the poly-A tail is hybridized. In alternative embodiments a single strand of complementary DNA that hybridizes to the 5'-UTR, open reading frame, and 3'-UTR of the mRNA, e.g. synthesized by reverse transcriptase. Subsequent removal of the DNA strand with DNases produces mRNA with 2'-modifications at its poly(A)-tail.

Where the acylation is selectively present on the poly-A tail, the region of the poly-A tail may comprise at least about 10%, at least about 20%, at least about 30%, at least about 50% acylated, at least about 75%, at least about 90% acylated 2'-OH, or more. The enhancement of translation may increase with the level of acylation.

Formulations

Compositions comprising modified RNA comprising acylated 2'-OH ribose are provided, where the RNA modification may be performed according to the methods disclosed herein. In some embodiments the RNA poly(A)-tail is selectively modified. In some embodiments the composition is formulated with a pharmaceutically acceptable excipient.

The modified RNA may be mRNA, tRNA, rRNA, viral RNA, synthetic RNA such as chemically synthesized or in vitro transcribed forms, or any other form of RNA, such as hnRNA and viroid RNA. An RNA acylated by the methods disclosed herein may comprise at least about 30% acylated 2'OH, at least about 50% acylated 2'OH, at least about 75% acylated 2'-OH, at least about 90% acylated 2'-OH, or more. Where the modification is selectively present in the poly (A)-tail, the RNA 5'-UTR, open reading frame, 3'-UTR of mRNA may be substantially free of acylated 2'OH, while the poly(A) tail may comprise at least about 30% acylated 2'OH, at least about 50% acylated 2'-OH, at least about 75% acylated 2'-OH, at least about 90% acylated 2'-OH, or more.

Formulations may be provided in a unit dosage form, where the term "unit dosage form," refers to physically discrete units suitable as unitary dosages for subjects, each unit containing a predetermined quantity of active agent in an amount calculated sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host. In some embodiments the unit dose is an effective amount for achieving a desired effect, for example, expression of a protein encoded by the modified mRNA.

The modified mRNA can be formulated with an a pharmaceutically acceptable carrier (one or more organic or inorganic ingredients, natural or synthetic, with which a subject agent is combined to facilitate its application). A suitable carrier includes sterile saline although other aqueous and non-aqueous isotonic sterile solutions and sterile suspensions known to be pharmaceutically acceptable are known to those of ordinary skill in the art.

The formulation may comprise, depending on the desired use, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the formulation may also include other carriers, adjuvants, or nontoxic, nontherapeutic, nonimmunogenic stabilizers and the like. In pharmaceutical dosage forms, the modified RNA may be provided in the form of pharmaceutically acceptable salts.

The RNA can be combined with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. “Pharmaceutically acceptable base addition salt” refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Depending on use and on the administration route, the modified RNA may be present in a unit dose at a range of from about 100 ng, 1 μg, 10 μg, 100 μg, 1 mg, 10 mg, 100 mg, 1 g, 10 g, 100 g, etc. Dosages will be appropriately adjusted for the desired use.

In some embodiments, pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). A carrier may bear the agents in a variety of ways, including covalent bonding either directly or via a linker group, and non-covalent associations. Suitable covalent-bond carriers include proteins such as albumins, peptides, and polysaccharides such as amino dextran, each of which have multiple sites for the attachment of moieties. The nature of the carrier can be either soluble or insoluble for purposes of the invention.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington’s Pharmaceutical Sciences 16th edition, Osol, A. Ed. (1980).

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the active agents can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. The data obtained from these cell culture assays and animal studies can be used in further optimizing and/or defining a therapeutic dosage range and/or a sub-therapeutic dosage range (e.g., for use in humans). The exact formulation, route of administration and dosage can be chosen by the individual physician in view of the patient’s condition.

The terms “subject,” “individual,” and “patient” are used interchangeably herein to refer to a mammal being assessed for treatment and/or being treated. In some embodiments, the mammal is a human. The terms “subject,” “individual,” and “patient” encompass, without limitation, individuals having a disease. Subjects may be human, but also include other mammals, particularly those mammals useful as laboratory models for human disease, e.g., mice, rats, etc. As used herein, the terms “treatment,” “treating,” and the like, refer to administering an agent, or carrying out a procedure, for the purposes of obtaining an effect on or in a subject, individual, or patient. Treating may refer to any indicia of success in the treatment or amelioration or prevention of a disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician.

Kits

Kits may be provided. Kits may include reagents suitable for modifying RNA, for example reagents for modification of 2'-OH groups of RNA with acylimidazole reagents and sulfonylation reagents. Components may be separately packaged in two or more containers suitable for use in the methods disclosed herein. Kits may also include tubes, buffers, etc., and instructions for use.

Kits may include DNA primer for hybridization to 5'- and 3'- untranslated regions in mRNA and coding sequences, for use in the selective modification of poly(A)-tails.

Kits may comprise water soluble organocatalysts that are a strong nucleophile and weak base for reversal of RNA acylation, e.g. N,N-dimethylglycinate; DABCO (1,4-diazabicyclo[2.2.2]octane), etc. Buffers for this purpose include, without limitation Tris (tris(hydroxymethyl)aminomethane), etc.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Chemically Reversible 2'-OH Acylation Protects RNA from Hydrolytic and Enzymatic Degradation Here, we develop an RNA preservation platform to enhance RNA in-solution and enzymatic stability. We demonstrated that 2'-OH acylation protects RNA from hydrolytic and enzymatic degradation. We also described the discovery of water-soluble organocatalysts that accelerate the reversal of acylation adducts and functionally restore RNAs. We further probe the hot spots for RNA in-solution and enzymatic degradation at the single-molecule, secondary structure, and nucleotide level, which reveals sequence and structure-based rules for mitigating hydrolytic and enzymatic RNA degradation. We also demonstrated that selected 2'-acylation can be spontaneously reversed upon and after transfection into cells with transfection reagents, restoring RNA biological functions such as translation. Together, our study demonstrates the utility of this platform for enhancing RNA stability, and provide mechanistic insights and a real-world solution for preserving RNAs regardless of their origin during storage and transportation.

Example 1

2'-OH Acylation Suppresses mRNA from Hydrolytic Degradation

Figure 2:
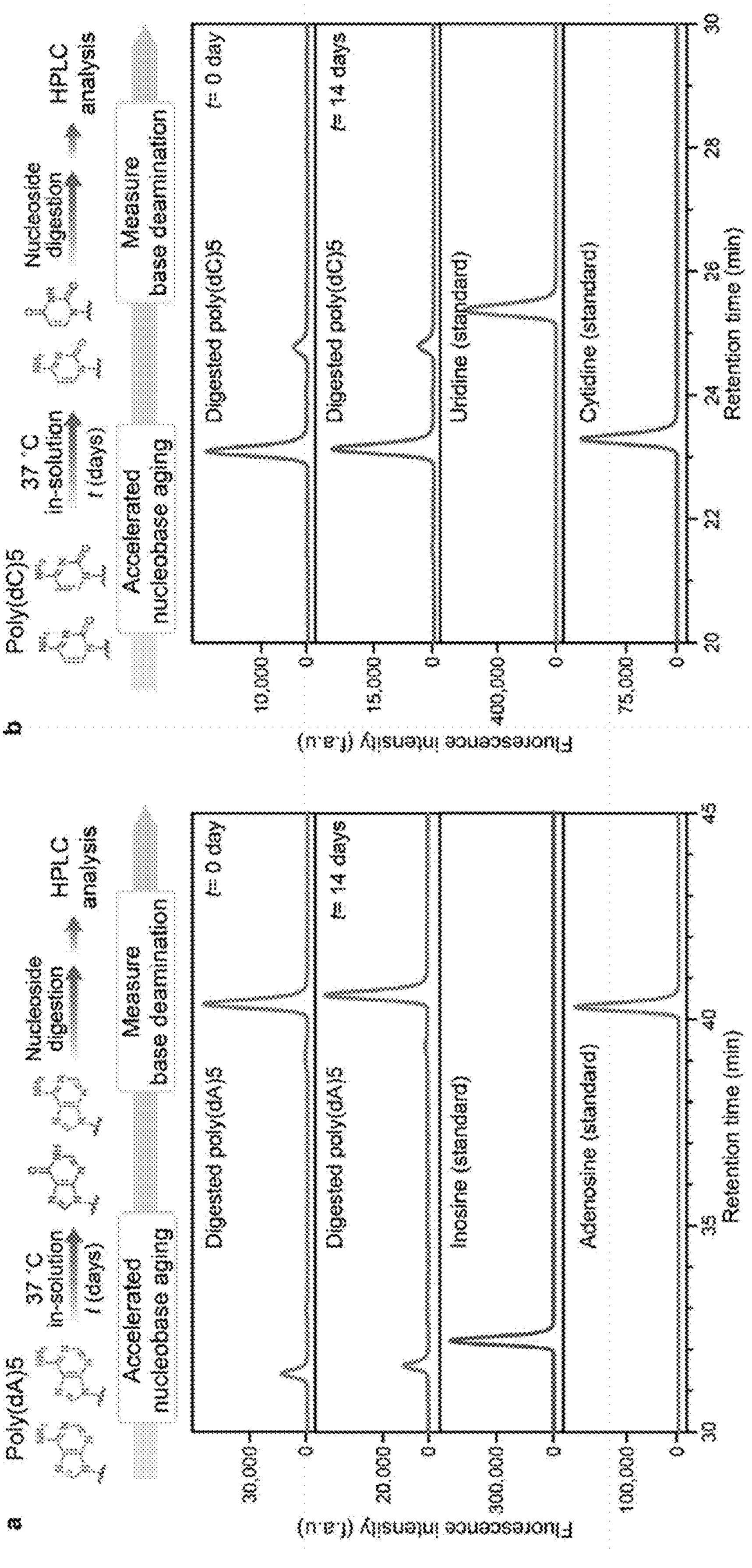
FIG. 2. HPLC showing undetectable deamination of adenosine and cytidine nucleobases during the course of this study.

In this example, the capacity to use this RNA cloaking strategy to stabilize RNA in solution was assessed with accelerated RNA aging experiments by incubating eGFP-mRNA species with or without cloaking with NAIN3 ((2-(azidomethyl)pyridin-3-yl)(1H-imidazol-1-yl)methanone) in RNase-free water at a mildly elevated temperature (37° C.) (FIG. 1). We then evaluated the lifespan of the mRNA by measuring the relative fraction of remaining fully intact RNA over time. Analysis by capillary electrophoresis (CE) of RNA fragments showed cloaking-dependent resistance to RNA degradation; for instance, intermediate cloaking (~50% of unpaired 2'-hydroxyls) extended the lifespan of intact eGFP-mRNA by -3-fold, while extensive cloaking (>90% of accessible 2'-hydroxyls) was capable of further shielding this RNA from thermal cleavage, extending mRNA lifespan by -7-fold. No damage to the nucleobases (e.g., deamination of adenine and cytosine) was observed within this timespan. Acylation-induced stabilization was further tested on a second, longer mRNA. As before, extensive cloaking (>90% of unpaired 2'-hydroxyls) also almost completely blocked backbone cleavage of Fluc-mRNA over six days in water (37° C.). No depurination of adenosine and cytidine was observed during the span of degradation experiments (FIG. 2). See, for example, FIG. 1. We also found that this applies to longer RNA (Fluc) and shorter sgRNA as well.

Example 2

Figure 3:
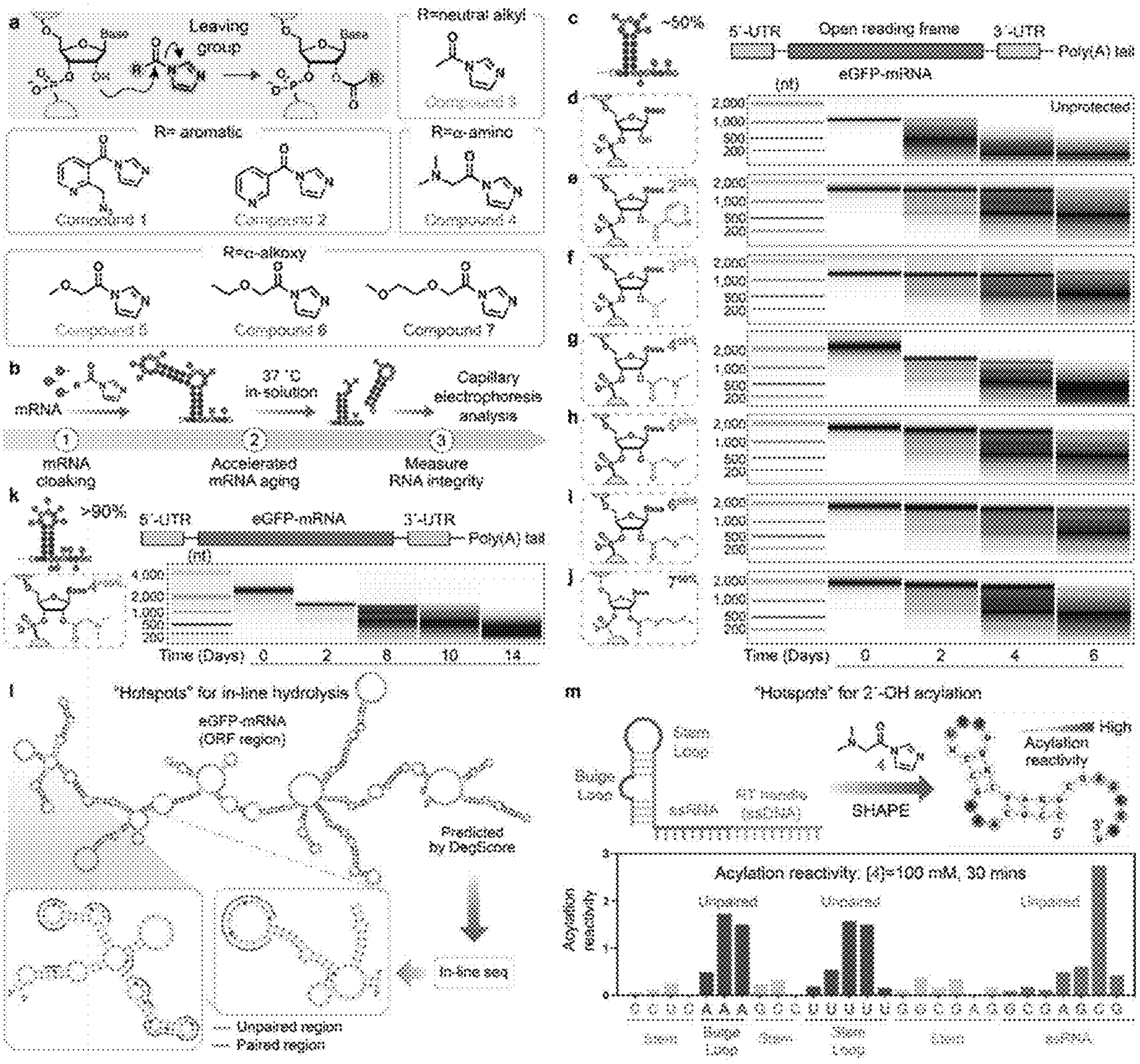
FIG. 3. Structurally diverse acylimidazole reagents enhance RNA stability in solution.

Structurally Diversed Acylimidazoles Protect mRNA from Hydrolytic Degradation In this example, we explored whether the physico-chemical features of acylimidazole reagents can affect their abilities to suppress RNA thermal degradation. We prepared a panel of six additional acylimidazole reagents containing structurally diversified substituents and compared them to the benchmark NAIN3 (FIG. 3). These library reagents were readily prepared with one-step activation of their corresponding low-cost carboxylic acids by 1,1'-carbonyldiimidazole. In the design of library compounds, we also paid attention to the installation of acyl groups with varied electrophilicity and size, which might later affect the nucleophile-promoted hydrolysis ("uncloaking") of acyl adducts to restore RNA. Desired features of acyl adducts include sufficient stability for RNA storage, while being reactive enough to uncloak efficiently. These structural features include aromaticity and a small acetyl group in selected reagents that makes acyl adducts more accessible to nucleophiles. We also installed a heteroatom (N or O) at the alpha carbon (Ca) to the carboxyl center of selected reagents, which may promote hydrolysis by electron-withdrawing induction with varied steric bulk. Because the maximum level of cloaking varied, we proceeded to equimolarly cloak RNA at ~50% of unpaired accessible 2'-hydroxyls of the model RNA to evaluate different reagents on RNA stability with similar levels of modification. We also noted that more structured RNA motifs were generally more difficult to cloak. All reagents do not react with the exocyclic amines of nucleobases and 5'-OH of RNA. Most reagents also do not react with 3'-OH.

Figure 4:
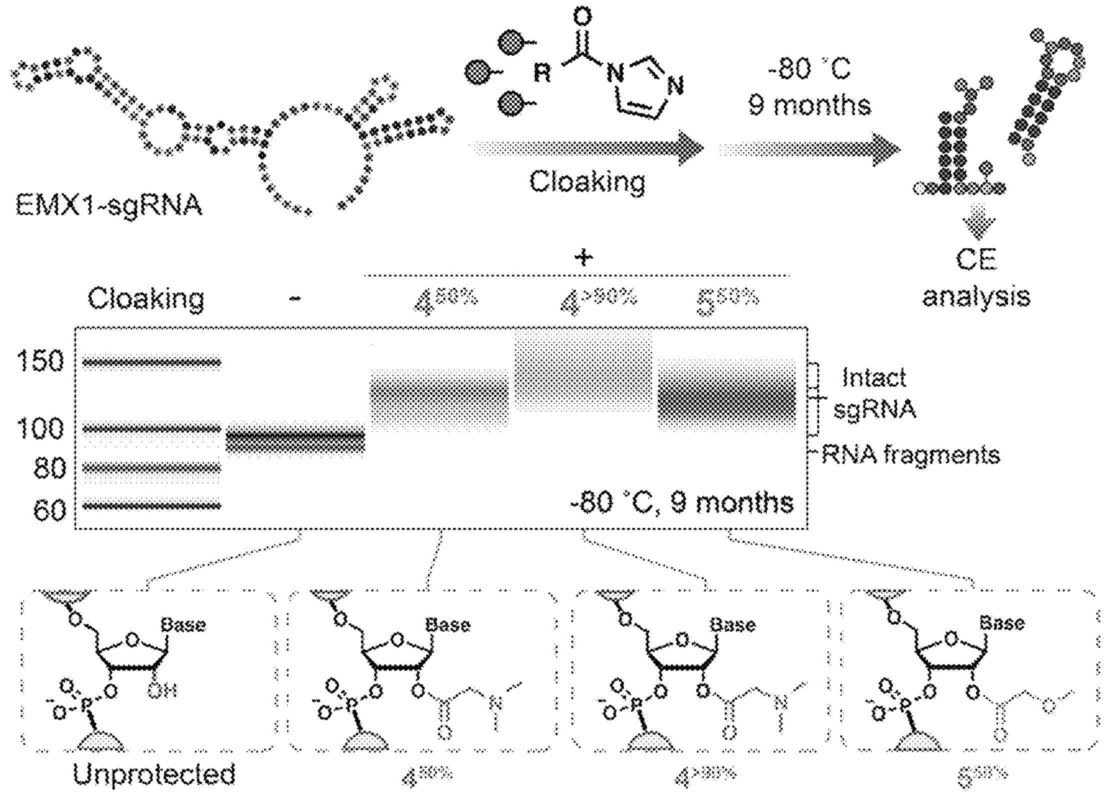
FIG. 4. Integrity of cloaked EMX1-sgRNA (105 nt) upon incubation in frozen RNase-free water after 9 months (−80° C.).

We screened these acylimidazole reagents for modulation of RNA thermal degradation by performing accelerated RNA aging experiments with eGFP-mRNA aliquots that were equivalently cloaked (~50% of unpaired accessible 2'-OH). Representative CE data are shown in FIG. 1 for cloaked eGFP-mRNA, which resisted thermal degradation across broad substituent types. The smallest (acetylimidazole) was notable as it attenuated RNA hydrolysis despite lacking a bulky substituent. Other active alkyl acylimidazoles also greatly augmented RNA's thermal stability, with ethoxyacetyl compound providing the most stability to eGFP-mRNA. Noting subtle differences in the stabilization, we hypothesized that the varying protection afforded by the reagents might arise from differential hydrolytic stability of their adducts; this was later confirmed (see below). For example, the slightly reduced enhancement of RNA thermal stability by N,N-dimethylglycine (DMG) acylimidazole is likely due to faster hydrolysis of DMG-ester at elevated temperatures, reflecting possible inductive effects and/or intramolecular general acid facilitation by its protonated tertiary amine. To compensate for this, more extensive cloaking by N,N-dimethylglycine (DMG) acylimidazole (>90% of unpaired accessible 2"-OH) extended the lifespan of eGFP-m RNA by ~5-fold. Similarly, cloaking with DMG acylimidazole led to enhanced stability in vitro transcribed EMX1-sg RNA over 9 months when stored at a low temperature (−80° C.) (FIG. 4).

Compounds tested resulted in the acyl adducts:

(1)

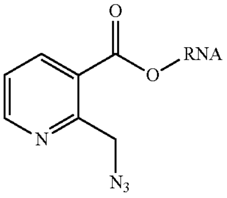

(2)

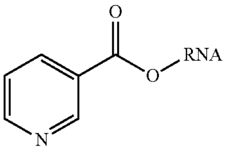

(3)

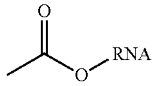

(4)

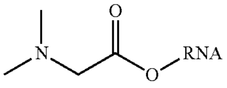

(5)

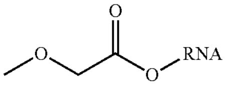

(6)

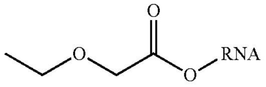

(7)

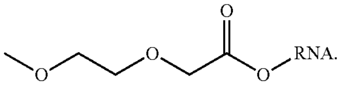

Aromatic R groups include:

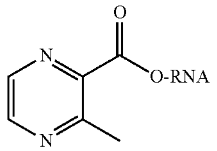

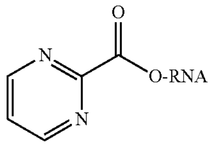

-continued

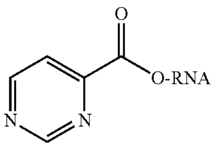

α-alkoxy adduct:

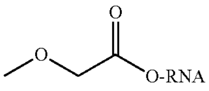

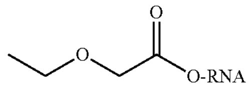

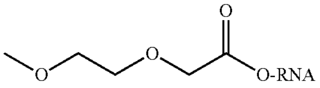

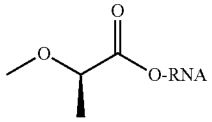

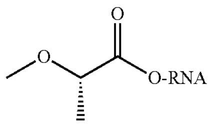

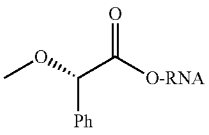

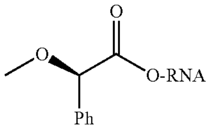

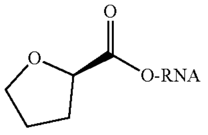

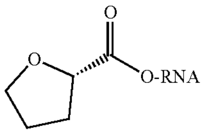

α-amino adduct:

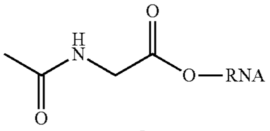

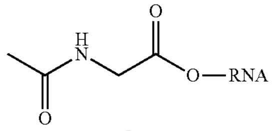

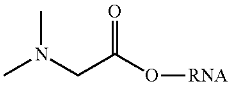

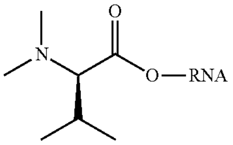

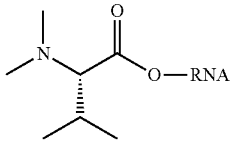

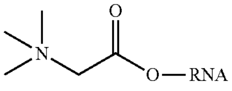

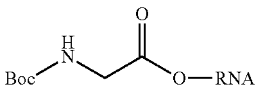

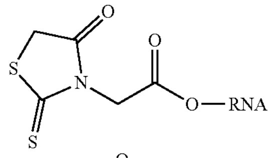

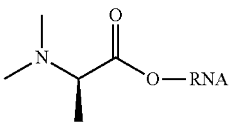

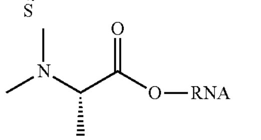

-continued

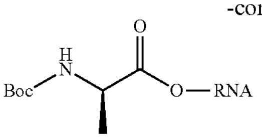
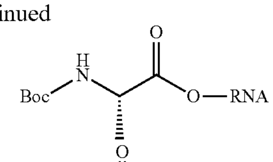
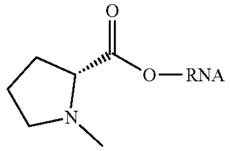
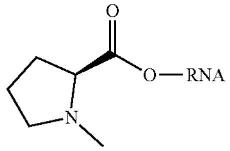
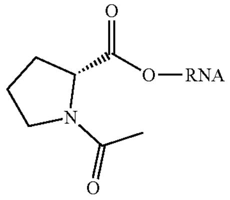
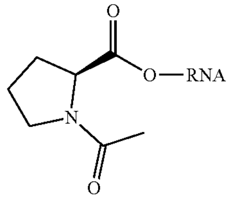
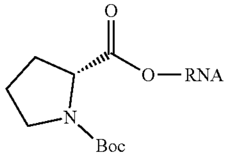
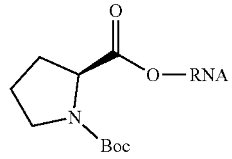

Glutathione-responsive adduct:

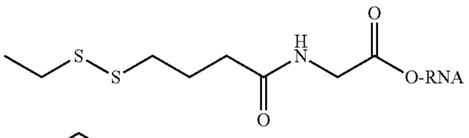
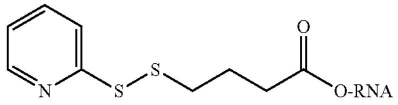

other candidate groups include:

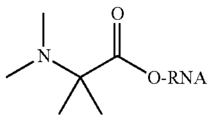
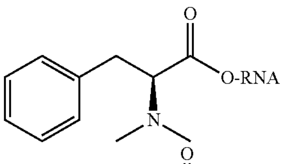
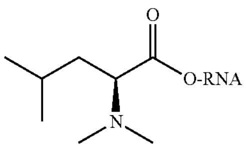
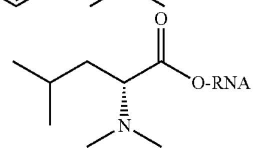
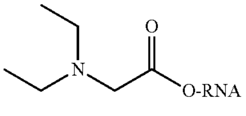

Example 3

Figure 5:
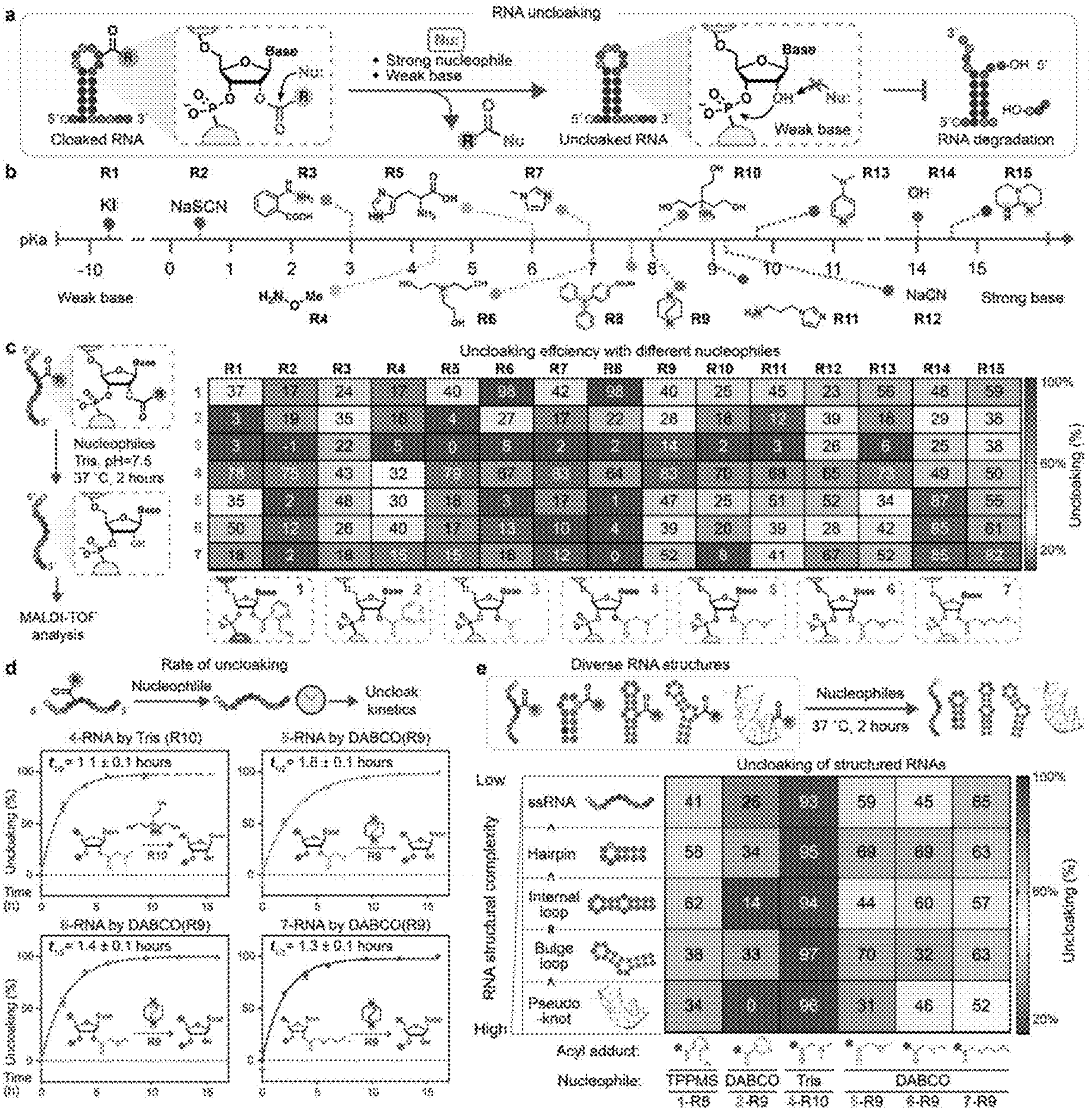
FIG. 5. Nucleophilic reagents remove 2'-polyacylation to uncloak RNA.

Organocatalytic and Spontaneous Removal of Acyl Protection for RNA Functional Recovery Nucleophiles are known to catalyze ester hydrolysis; examples include the use of imidazole and pyridine as nucleophilic catalysts. To restore biological activity of RNAs after cloaking-based stabilization, we tested uncloaking strategies to promote rapid hydrolysis of 2'-carboxyl esters with weakly basic nucleophiles (FIG. 5). In this example, we assembled a panel of 13 reagents that were known as strong nucleophiles or promoters of ester hydrolysis, with pKa values ranging from −10 to 9.7. In the library design, we avoided the use of strong Bronsted bases to prevent hydrolytic RNA backbone cleavage. Nucleophiles were screened against the 18nt model RNA containing acyl groups of each type at 37° C. and neutral pH, which identified at least 9 sensitive acylation-nucleophile pairs that promoted >50% removal of adducts within 2 hours. Among these, acyl adducts by NAIN3 can be reversed via Staudinger reaction, although we previously found this reversal strategy cannot be readily adapted for long RNA (>600 nt). Other adducts can also be rapidly removed with designated nucleophiles, with half-lives for reversal ranging from 1.1 to 1.8 hours. Adducts by nicotinic acid and acetyl acylimidazole derivatives are relatively resistant to reversal by nonbasic nucleophiles and were no longer pursued.

In this embodiment, we show that the sensitivities of 2'-acyl adducts towards each nucleophile correlate with their physico-chemical properties. Aliphatic adducts showed distinct sensitivities towards library nucleophiles. For 2'-acyl adduct by DMG, the effects of the biocompatible tris(hydroxymethyl) aminomethane (Tris) buffer alone were substantial, consistent with previous reports that Tris can hydrolyze active esters. Interestingly, and in contrast, the simple acetyl adducts by acetylimidazole were not reversed by Tris, nor by any of the other conditions tested, suggesting that the electron-withdrawing heteroatom at the α-carbon of DMG-derivative sensitizes the ester for hydrolysis. Notably, alkoxyesters displayed major differences in their vulnerabilities towards nucleophiles compared to the DMG ester, further showing that substituents at the α-carbon can significantly modulate an ester's susceptibility towards nucleophiles.

Example 4

Figure 6:
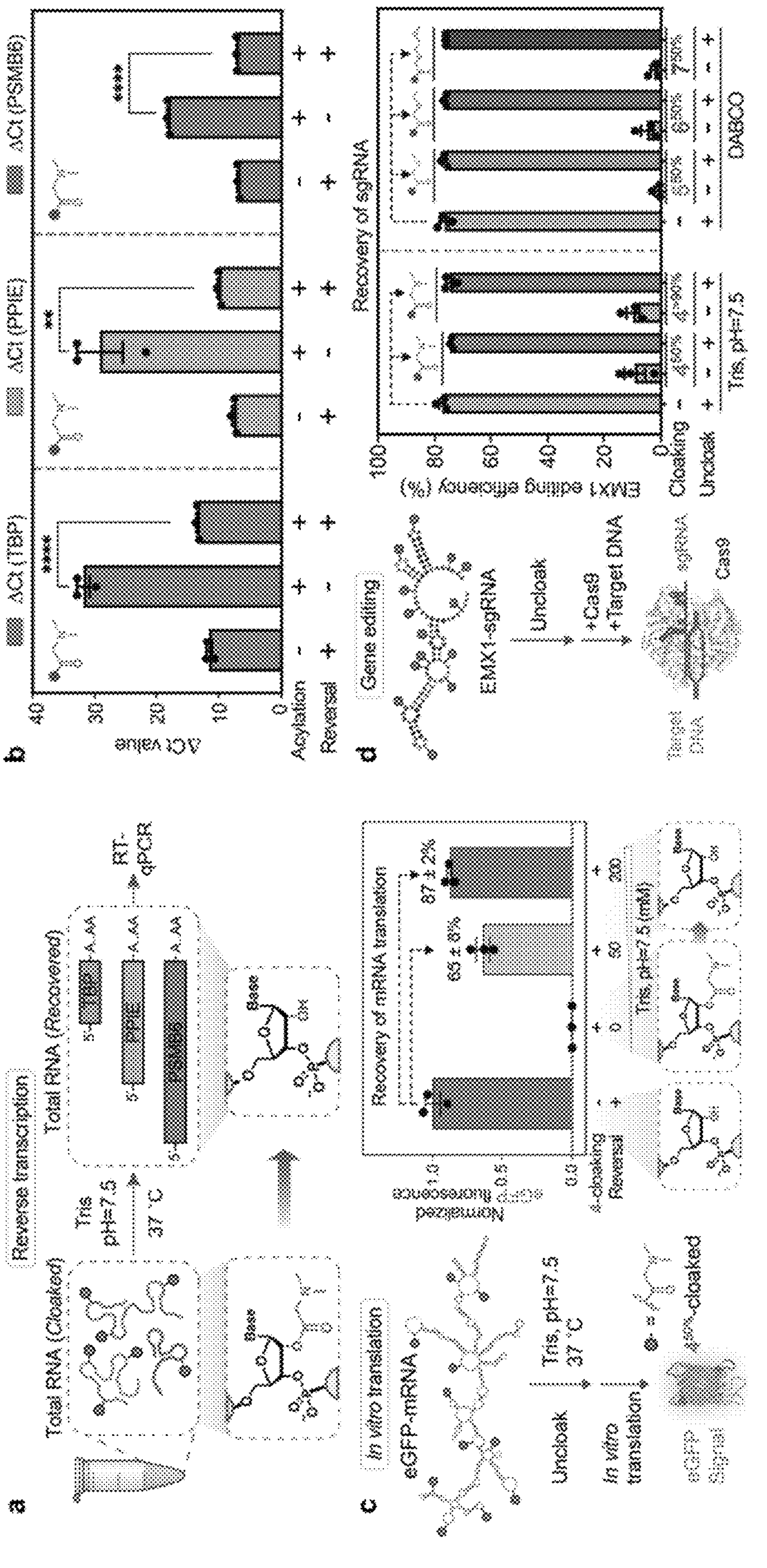
FIG. 6. Nucleophile-promoted RNA uncloaking restores RNA functions.

Nucleophile-Promoted RNA Uncloaking Restores RNA Functions (FIG. 6)

In this example, we demonstrate the capacity of nonbasic nucleophilic reagents to recover RNAs while keeping the RNA strands intact and functional. For instance, the ability of a single 2'-acylation to halt reverse transcriptase during primer extension necessitates efficient 2'-deacylation to avoid premature reverse transcription termination. Considering that DMG acylimidazole can maximally protect long RNAs against a broad range of RNases and demonstrates the fastest reversal kinetics, we assessed whether these nucleophiles could restore reverse transcription (RT) of DMG-cloaked RNA. We isolated and cloaked total cellular RNA from HEK293 cells with DMG acylimidazole, and recovery efficiency was evaluated for three representative mRNAs by the reverse transcription efficiencies. RT-qPCR results in FIG. 4 showed that incubation with Tris alone at neutral pH reinstated the reverse transcription of the cloaked mRNAs (TBP, PPIE, and PSMB6) after 24 h, regardless of their transcript and amplicon lengths. Additionally, the restored cellular RNA can remain largely intact and demonstrated similar or the same ΔCt values compared to their unprotected counterparts, establishing that RNA uncloaking by Tris is biocompatible for effective recovery of reverse transcription of diverse RNAs. Recent experiments have shown that local 2'-acylation can terminate translation when introduced into the coding region of mRNAs. Thus, we investigated whether Tris could restore the translation of a model eGFP-mRNA densely cloaked (50%) by DMG acylimidazole. Based on in vitro translation assays, cloaking with DMG acylimidazole strongly blocked the translation of eGFP-mRNA, while treatment with Tris, pH=7.5 at 37° C. rendered up to 87% restoration of eGFP expression (FIG. 4). Electrophoresis experiments showed that the mRNA integrity remained largely unchanged after uncloaking. These data suggested that Tris alone can recover mRNA translation of adducts of DMG acylimidazole, while keeping the RNA intact. To explore the generality of this observation, we applied the methods to an in vitro transcribed CRISPR sgRNA. Acylation of EMX1-sgRNA by other reagents blocked its cleavage function (<10%) in vitro. Treatment of cloaked sgRNA with Tris (for DMG-cloaked sgRNA) or 1,4-diazabicyclo[2.2.2]octane (DABCO) (for alkoxy acylimidazole-cloaked sgRNA) at neutral pH for 11 hours fully restored DNA cleavage, while sgRNA remained largely undegraded.

Example 5

Figure 7:
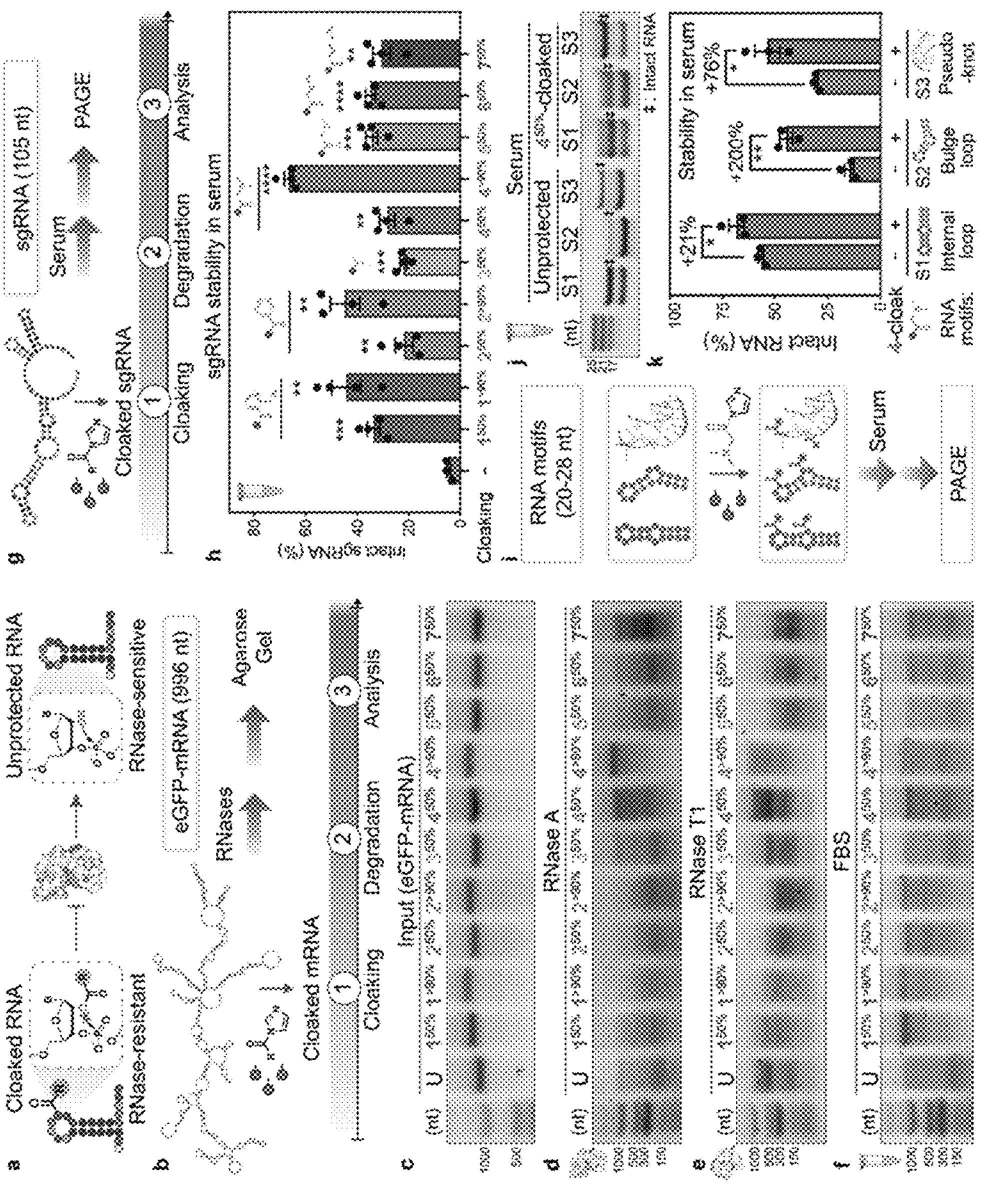
FIG. 7. RNA cloaking suppresses enzymatic RNA degradation by RNases and biofluids.
Figure 8:
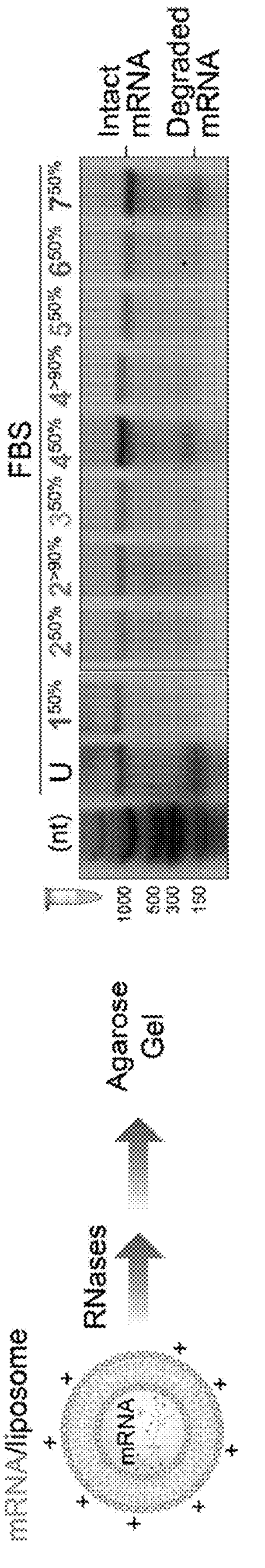
FIG. 8. Representative agarose gel showing the impacts of LNP formulation by lipofectamine on serum stability of cloaked eGFP-mRNA in vitro.

2'-OH Acylation Suppresses mRNA from Enzymatic Degradation by RNases, Mammalian Lysates, and Serum In this example, we systemically surveyed protective effects of cloaking with representative RNases and biofluids, recapitulating the common enzymatic conditions RNAs encounter during storage, handling, and application (FIG. 7). We found that cloaking with DMG acylimidazole effectively shielded cleavage sites on eGFP-mRNA from nucleolytic degradation by RNase A—the prototypical member of RNase A superfamily abundant in vertebrate tissues, and RNase T1—a representative ssRNA-cleaving endonuclease. In contrast, other acylating reagents did not sufficiently protect the mRNA against recombinant RNases. We next evaluated whether cloaking could ameliorate mRNA degradation in fetal bovine serum (FBS), a frequent component of eukaryotic cell culture (FIG. 8). The serum stability of DMG-cloaked eGFP-mRNA is on par with the stability of LNP-formulated mRNA. This is likely due in part to DMG acylimidazole retaining RNA secondary structures and helicity for maximum resistance to RNases. Acylating reagents also protect eGFP-mRNA against FBS to varying degrees. We also showed that cloaking is compatible with formulation with LNP at least transiently, which together can almost fully shield mRNA from degradation in serum. Thus, 2'-acylation provides context-dependent protection of long RNA (e.g., mRNA) against ribonucleolytic enzymes. Reagent DMG acylimidazole effectively shields mRNA against a broad range of RNases.

Example 6

2"-OH Acylation Suppresses sgRNA from Enzymatic Degradation by Serum

In this example, we systematically characterized how acylimidazoles affect enzymatic degradation of EMX1-sgRNA in serum, a 105nt single guide RNA (sgRNA) for CRISPR-Cas9 gene editing (FIG. 7). In general, we found that an increased level of cloaking led to higher serum resistance. Among all reagents, DMG acylimidazole enhanced sgRNA stability the most, by up to 14-fold. Unlike long RNAs, sgRNA was also effectively protected against serum by other acylating reagents with 7-10-fold increases in serum stability. Although such protection most likely extends to other RNAs, the secondary structures of RNA may influence the magnitude of enhancement in enzymatic stability. For example, reagent DMG acylimidazole increases the serum stability of a bulge loop RNA motif and a structurally complex pseudoknot, while having minimal enhancement in serum stability for an internal loop motif. This is likely due in part to different RNA motifs having distinct "hotspots" for enzymatic degradation, which may not be completely shielded by cloaking. Taken together, 2'-acylation effectively enhances the serum stability of RNA, the magnitude of which may be influenced by the length and structure of the underlying RNA.

Example 7

Mechanism of How 2'-OH Acylation Suppresses mRNA from Hydrolytic and Enzymatic Degradation (FIG. 3).

In this embodiment, a machine learning-based algorithm (DegScore) and in-line sequencing suggested that the "hotspots" of thermal degradation in eGFP-mRNA locate mainly in its unpaired regions. Concomitantly, selective 2'-hydroxyl acylation analyzed by primer extension (SHAPE) indicated that the "hotspots" of cloaking by acylating reagent (e.g., DMG acylimidazole) also primarily occur at unpaired sequences of RNA. This colocalization of "hotspots" for degradation and cloaking likely contributes to the stabilizing effect by 2'-acylation. Taken together, the data confirm that ester adducts of acylimidazoles block RNA thermal degradation, and this general stabilizing effect appears to be independent of size and aliphatic versus aromatic construction.

Example 8

Figure 9:
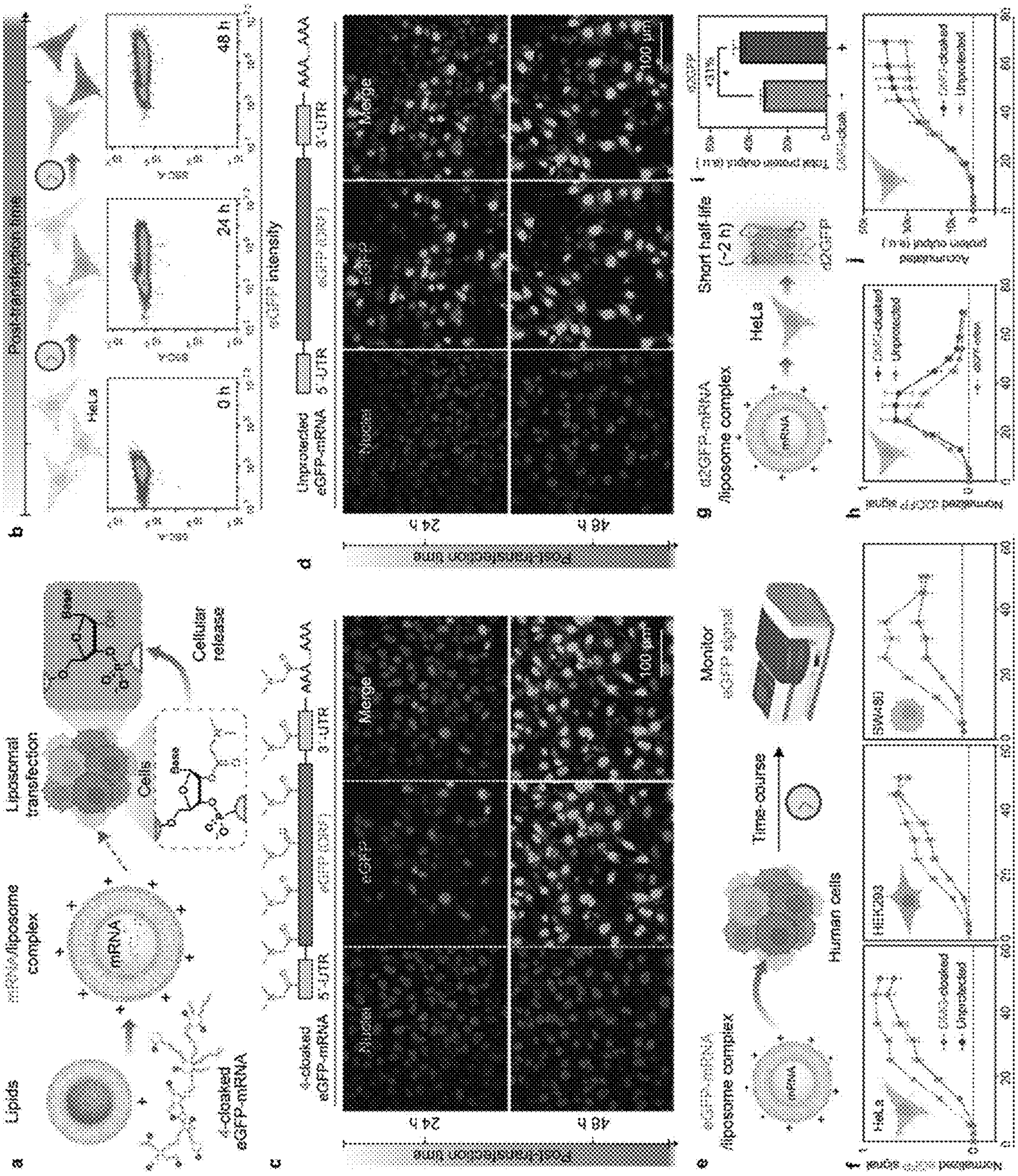
FIG. 9. Spontaneous RNA uncloaking restores mRNA translation with extended functional half-lives in human cells.

Spontaneous RNA Uncloaking in Human Cells Restores mRNA Translation with Extended Functional Half-Lives (FIG. 9)

Intact cells maintain high intracellular concentrations of nucleophilic species such as cysteine and glutathione. The sensitivity observed here of 2'-carboxyl esters towards nucleophilic hydrolysis suggests possibility of spontaneous RNA uncloaking both during and after cellular delivery, which might enable RNA functional recovery. In this example, we employed cloaked mRNAs encoding fluorescent reporter proteins. Indeed, we observed the emergence of strong green fluorescence signals by flow cytometry over a period of two days in HeLa cells transfected with intermediately DMG-cloaked eGFP-mRNA. Single-blind fluorescence imaging further confirmed that the translation of DMG-cloaked eGFP-mRNA was restored after an initial delay compared to its unprotected counterpart, corroborating the spontaneous RNA uncloaking in live cells. In marked contrast, for eGFP-mRNA that was cloaked with NAIN3, translation remained strongly inhibited. This further confirmed that the recovery of eGFP expression is due to the releasing properties of DMG-ester, and testing in two additional cell lines (SW480, HEK293) confirmed generality. Moreover, the delayed translation of cloaked mRNAs reflects an initial uncloaking step, which when occurring over time may provide slow-release translation kinetics—reducing an early expression peak and extending the duration of translation (see below). Finally, we also observed that translation of eGFP-mRNA with alkoxyl acyl adduct can also be restored in cells, highlighting possible control over mRNA release kinetics by modification of the acyl group.

Example 9

Spontaneous RNA Uncloaking of Selected Acylimidazole Reagent in Human Cells Extended mRNA Functional Half-Lives (FIG. 9)

In this example, we demonstrated how cloaking affects the functional lifespan of mRNA in cells. Because eGFP protein is highly stable with a half-life >24 hours, protein degradation alone dominates expression and provides no information about mRNA functional half-lives. We therefore adopted a reporter system employing mRNA encoding a destabilized green fluorescent protein d2GFP, where both mRNA and protein degradation occur with similar half-lives of ~2-3 hours. We observed that the translation of unprotected d2GFP-mRNA quickly descended after peaking. In contrast, intermediate cloaking by DMG acylimidazole led to sustained d2GFP-mRNA translation at its peak level for ~10 hours, strongly suggesting its ability to extend the functional lifespan of d2GFP-mRNA effectively. This extended mRNA functional half-life also enhanced the total protein output of d2GFP-mRNA by 31% in HeLa cells and this enhancement became increasingly prominent after ~31 h post-transfection compared to unprotected d2GFP-mRNA. Taken together, RNA cloaking by DMG derivative DMG acylimidazole effectively extended d2GFP-mRNA functional lifespan and translation, providing insights for the potential use of reversible 2'-acylation as a modulator of mRNA translation kinetics.

Figure 10:
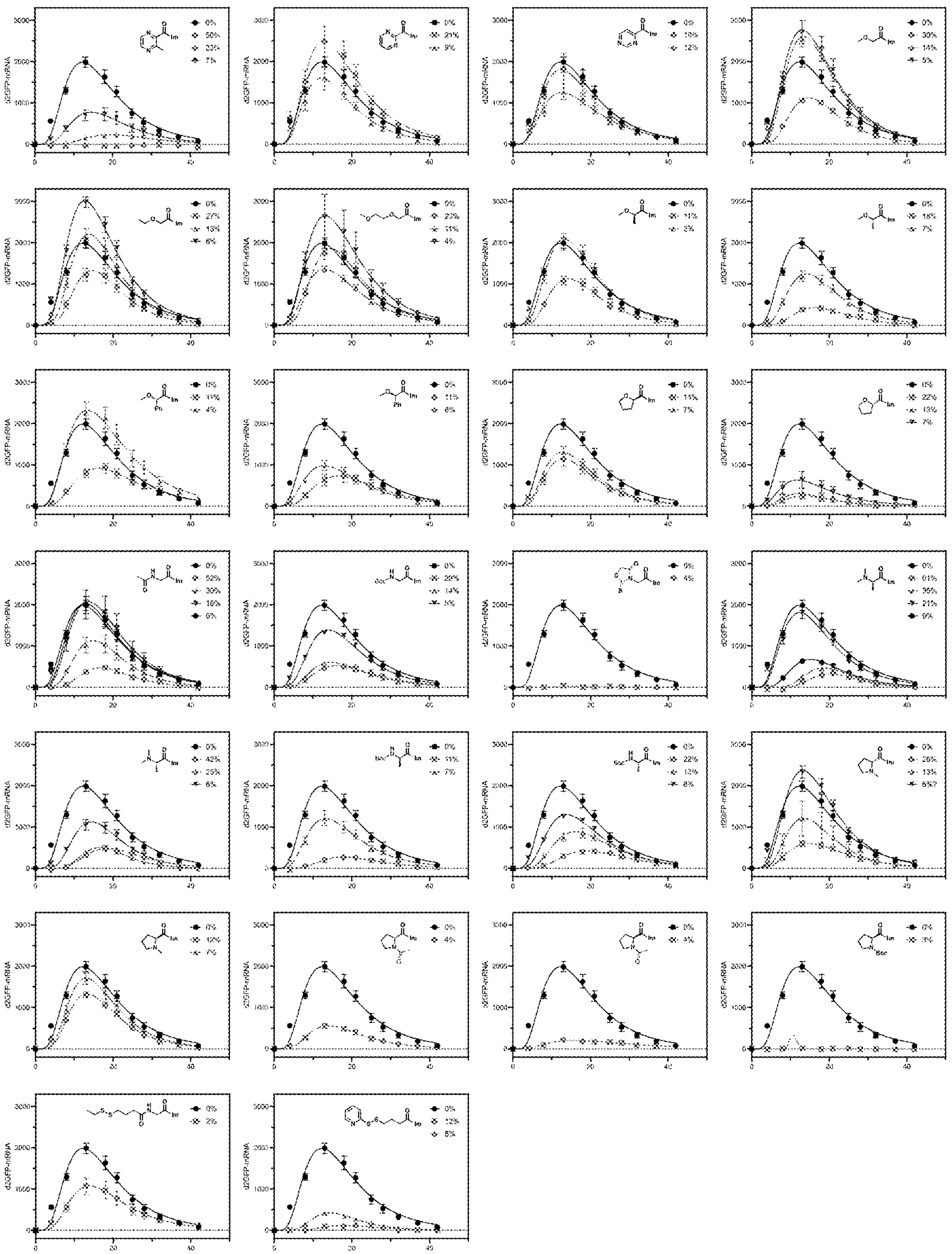
FIG. 10. Spontaneous RNA uncloaking of selected acylimidazole reagent in human cells extended mRNA functional half-lives.

We further demonstrated an additional panel of acylimidazole reagents allowed spontaneous RNA uncloaking in human HEK293 cells to restore mRNA translation with extended functional half-lives (FIG. 10).

Example 10

Figure 11:
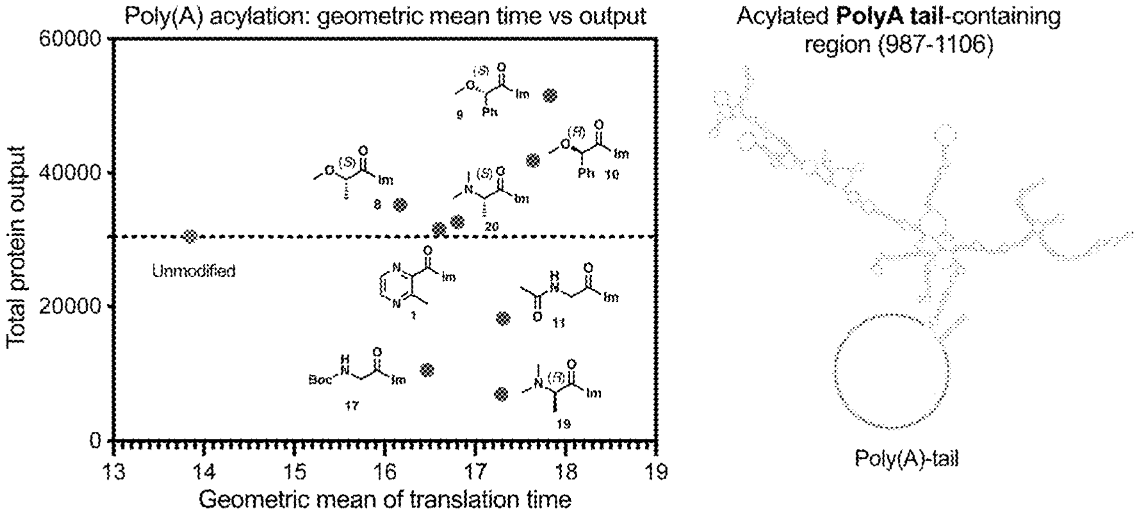
FIG. 11. Chemical modification at 2'-OH groups of mRNA poly(A)-tail with acylimidazoles, sulfonyltriazole, or sulfonylimidazole reagents extended mRNA functional half-lives and modulated total protein output.

Chemical Modification at 2'-OH Groups of mRNA Poly(A)-Tail with Acylimidazoles Reagents Extended mRNA Functional Half-Lives (FIG. 11).

In this example, we used the DNA tiling method as reported in Angewandte Chemie 133.51 (2021): 27002-27009 to perform localized 2'-acylation at Poly(A)-tail of d2GFP-mRNA. To do this, the 5'-UTR, open reading frame, 3'-UTR of mRNA were hybridized with complementary DNA oligos, with a length ranged from about 18 nt to about 120 nt. The mRNA-DNA hybrids were then reacted with acylimidazole reagents shown in FIG. 9 to selectively modify 2'-OH groups within the Poly(A)-tail of mRNA. We found that multiple a-alkoxy acylimidazoles were capable of extending the translation lifespan of d2GFP-mRNA, suggesting enhanced in-cell mRNA stability. Concomitantly, the total protein output of d2GFP-mRNA was increased up to about 80% in HEK293 cells. In contrast, a-amino- and a-amide- acylimidazoles decreased the total protein output of d2GFP-mRNA, although extending the mRNA translation time. 2'-Acylation by methyl pyrimidine acylimidazole allows delayed d2GFP-mRNA translation with equivalent total protein output, as compared to the unmodified d2GFP-mRNA.

Example 11

Chemical Modification at 2'-OH Groups of mRNA Poly(A)-Tail with Sulfonyltriazole or Sulfonylimidazole Reagents Extended mRNA Functional Half-Lives In this example, we use the DNA tiling method as reported in Angewandte Chemie 133.51 (2021): 27002-27009 to perform localized 2"-acylation at Poly(A)-tail of d2GFP-mRNA. To do this, the 5'-UTR, open reading frame, 3'-UTR of mRNA are hybridized with complementary DNA oligos, with a length ranged from about 18 nt to about 120 nt. The mRNA-DNA hybrids are then reacted with sulfonyltriazole or sulfonylimidazole reagents to selectively modify 2'-OH groups within the Poly(A)-tail of mRNA. mRNA with 2'-sulfonylation at its poly(A)-tail can have extended mRNA functional half-lives. mRNA with modified poly(A)-tail can have enhanced total protein output depending on the chemical structures of sulfonyltriazole or sulfonylimidazole.

Example 12

Chemical Modification at 2'-OH Groups of mRNA Poly(A)-taTil Enhances mRNA Translation In this example, the polyA tail of a messenger RNA was selectively modified with acyl groups that increase levels of protein expression. To achieve this, the majority of the mRNA was temporarily protected from acylation by hybridizing oligodeoxynucleotides (oligos) to it, leaving the polyA tail unhybridized and accessible for acylating agents to modify it.

The 5'-UTR, open reading frame, and 3'-UTR of d2GFP-mRNA were hybridized with complementary DNA oligos, with a length ranging from about 18 nt to about 120 nt. Specifically, 2 μL of 1 μg/μl of d2GFP-mRNA (6 pmol) was mixed with 12 μL of pooled complementary DNA oligos (12 pmol each), 1.88 μL of 500 mM NaCl, and 2.92 μL of RNase-free water. The resulting mixture was heat denatured at 70° C. for 4 minutes, then stepped down to 4° C. at 1° C./second. To it was added a 3.3×MOPS buffer (333 mM MOPS, 20 mM $MgCl_2$, 333 mM NaCl, pH=7.5) and incubated at 4° C. for 15 minutes. The mRNA-DNA hybrids were then reacted with acylimidazole reagents (shown below) to selectively modify 2'-OH groups within the Poly (A)-tail of d2GFP-mRNA. Specifically, 3.34 of 10× acylimidazole solution were added to the mRNA-DNA hybrids. The resulting solution was incubated at 4° C. for 2 hours.

Compounds tested resulted in the acyl adducts:

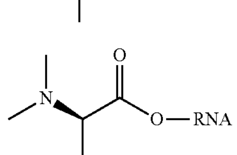
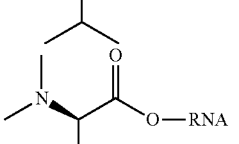
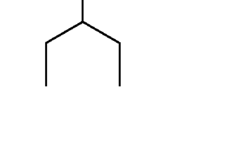
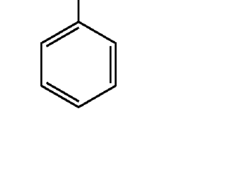

-continued

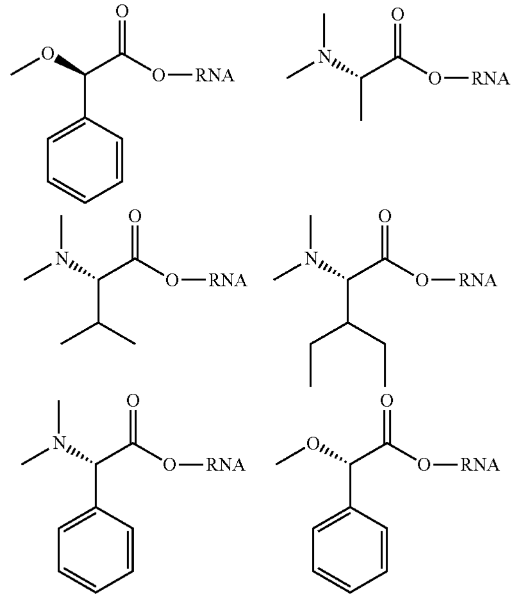

The acylated mRNA-DNA duplexes were then purified with RNA MagClean Dx beads. Specifically, 59.6 μL (1.8× by volume) of RNA MagClean Dx Beads was added to each reaction. The suspension was pipetted ten times to mix and then incubated at room temperature for 5 minutes. The reaction tube was transferred onto a magnetic rack and sat for 8 minutes. The supernatant was aspirated and discarded. The beads were then washed with 200 μL of 70% ethanol and incubated at room temperature for 30 seconds. The supernatant was aspirated and discarded. The washing step was repeated for a total of three times. The beads were air-dried for 10 minutes at room temperature off the magnetic plate. To elute the mRNA-DNA duplex, 25 μL of RNase-free water was added. The suspension was pipetted ten times to mix and then transferred onto a magnetic rack. The supernatant was then collected for DNaseI treatment.

To remove the protective DNA oligos, 25 μL of mRNA-DNA solution was mixed with 4.1 μL of 10× DNase I buffer and 12 μL of RQ1 RNase-free DNase. The reaction mixture was incubated at 37° C. for 1 hour. The final poly(A)-modified d2GFP-mRNA was purified with RNA Cleanup & Concentrator Column-5 according to the manufacturer's protocol.

Figure 12:
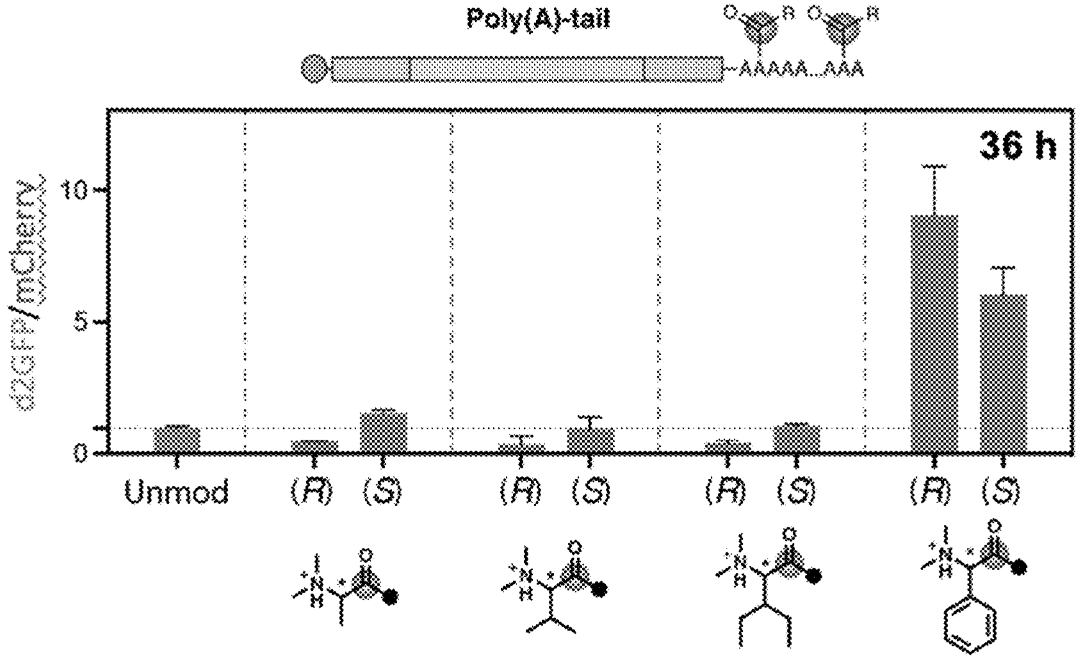
FIG. 12. α-Phenyl substituted acylimidazole reagents enhanced the protein production of d2GFP-mRNA.
Figure 13:
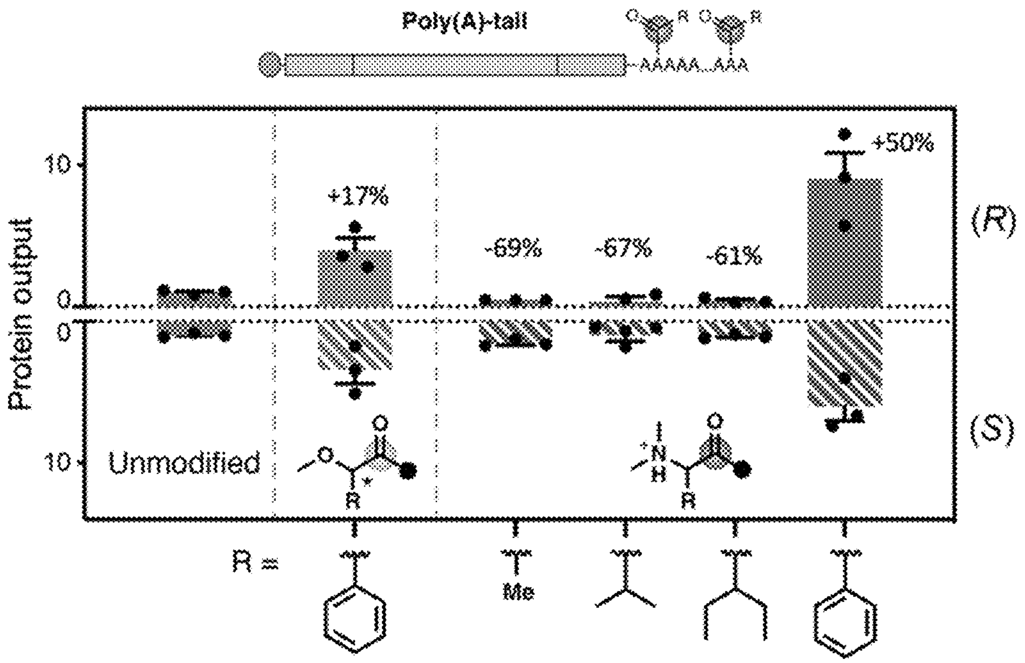
FIG. 13. The chirality of acylimidazole reagents affects their influence on protein production.
Figure 14:
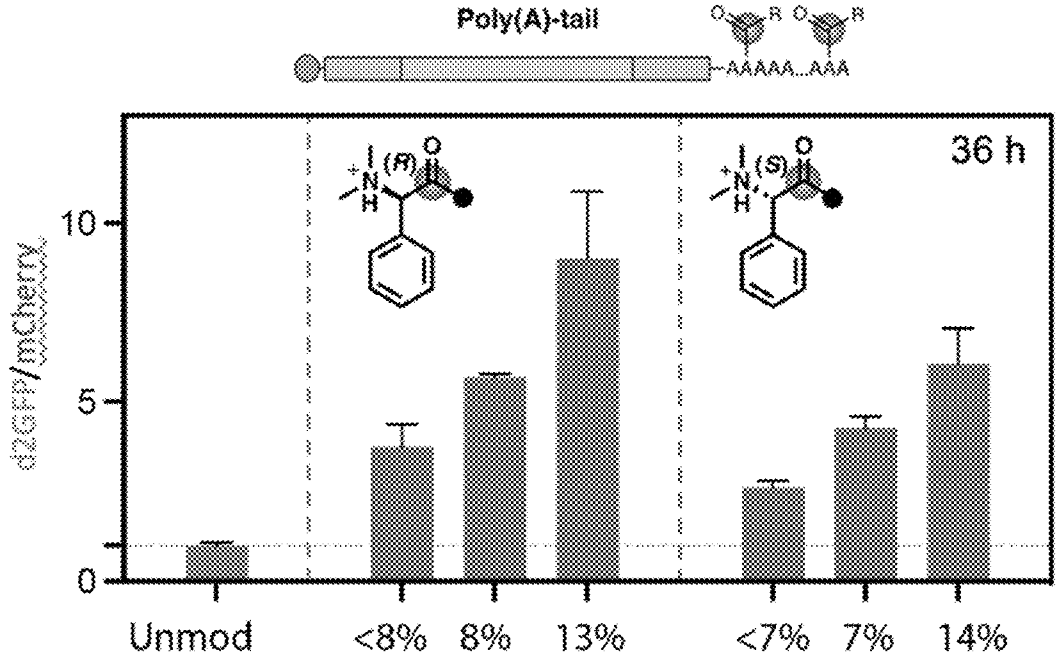
FIG. 14. Dose-dependent enhancement of mRNA translation by poly(A)-modification. The level of 2'-OH acylation was annotated as percentages.

To evaluate the translation of poly(A)-modified d2GFP-mRNA, 80 ng of poly(A)-modified d2GFP-mRNA and 20 ng of mCherry-mRNA were cotransfected into HEK293 cells on a 96-well plate using Lipofectamine Messenger-MAX. A microplate reader monitored the translation of d2GFP-mRNA and mCherry over time. We observed that α-phenyl substituted acylimidazole reagents enhanced the protein production of d2GFP-mRNA by up to 8-10 fold (FIG. 12). In contrast, acylimdazoles with alkyl substituents at the a-carbon failed to enhance the protein translation. The chirality of acylimidazole reagents also affects their effects on protein production (FIG. 13). For example, for α-phenyl substituted acylimidazoles, the R configuration of acyl adducts led to a 17-50% increase in protein production compared to their S counterparts. Furthermore, poly(A)-modification enhances protein output in a dose-dependent fashion (FIG. 14). Increasing the number of 2'-acyl adducts at the poly(A)-tail demonstrated dose-dependent enhancement of d2GFP expression.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method for reversible protection of RNA in aqueous solution, the method comprising:

(a) contacting, in aqueous solution, RNA with an acylimidazole in an effective dose and for a period of time sufficient to generate modified RNA comprising ribose acylated at the 2' OH position wherein the acylimidazole has the structure:

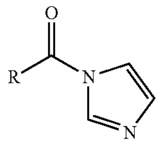

wherein R is selected from

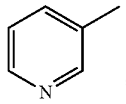

, $CH_3$,

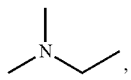

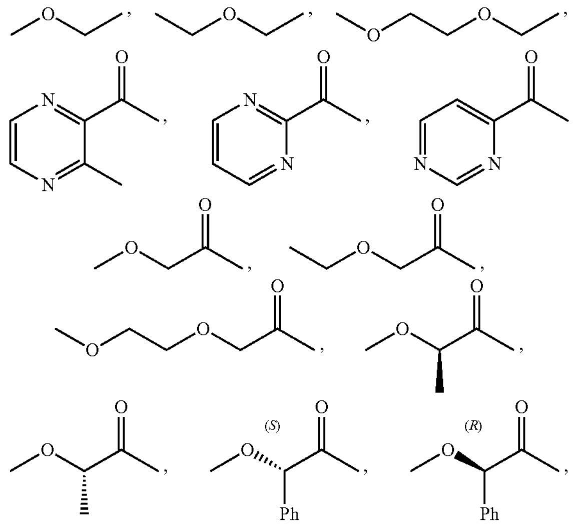

-continued

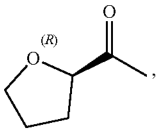
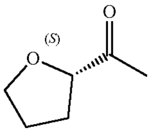
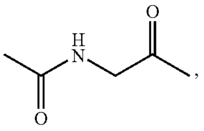
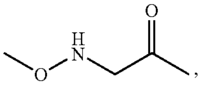
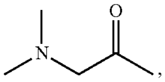
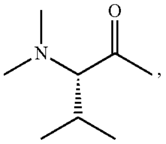
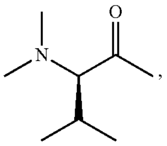
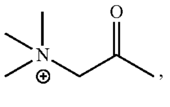
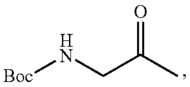
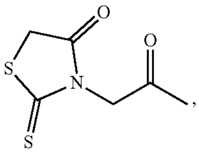
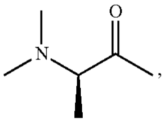
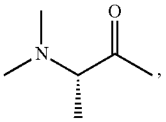
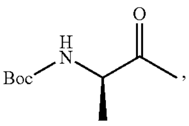
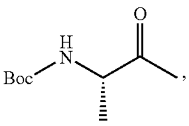
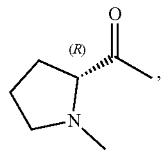
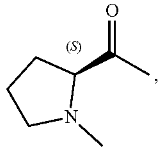
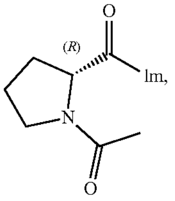
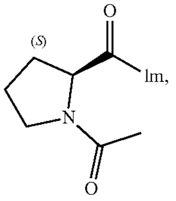
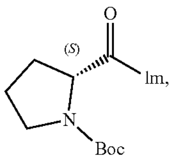
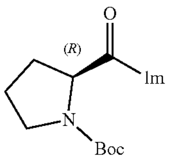
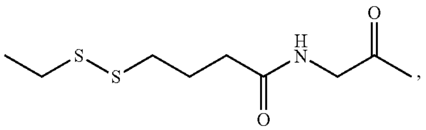
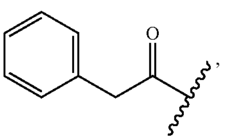
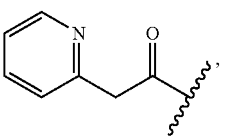
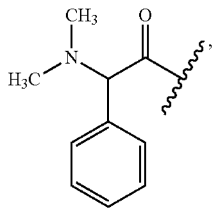
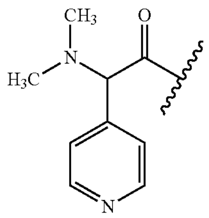

-continued

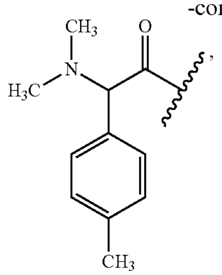
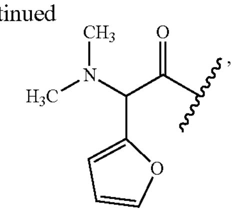
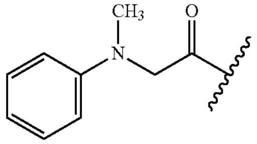
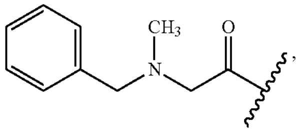
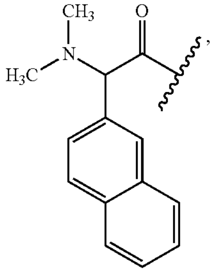
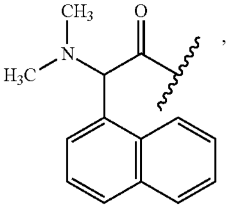
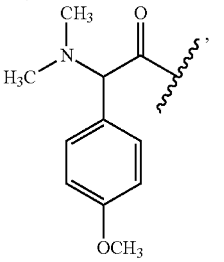
and
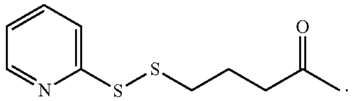

2. A method for reversible protection of RNA in aqueous solution, the method comprising:

(a) contacting, in aqueous solution, RNA with a sulfonylation agent in an effective dose and for a period of time sufficient to generate modified RNA comprising ribose sulfonated at the 2' OH position, optionally where the sulfonylation agent is a sulfonylimidazole or sulfonyltriazole; and (b) optionally, after a desired period of time, reversing the acylation with a water soluble organocatalyst, performed in aqueous solution at neutral pH.

3. The method of claim 2, wherein the sulfonylation agent has the structure:

II

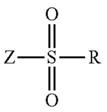

where R is a substituted or unsubstituted alkyl group, a substituted or unsubstituted heteroalkyl group, a substituted or unsubstituted aryl or heteroaryl, a substituted or unsubstituted cycloalkyl; and Z is imidazole, 1,2,3-triazole, or 1,2,4-triazole.

4. The method of claim 3, wherein R is:

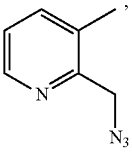,
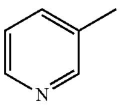,
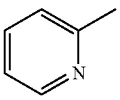, or
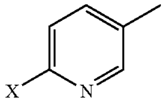, where X is Cl, Br, or $CH_3$.

5. A method for reversible protection of RNA in aqueous solution, the method comprising:

(a) contacting, in aqueous solution, RNA with an acylimidazole in an effective dose and for a period of time sufficient to generate modified RNA comprising ribose acylated at the 2' OH position; and (b) after a desired period of time, reversing the acylation with a water soluble organocatalyst, performed in aqueous solution at neutral pH, wherein the RNA is mRNA, and where the poly(A) tail of the mRNA is selectively acylated.

6. The method of claim 5, wherein translation of the selectively acylated mRNA in enhanced at least 5-fold relative to unmodified mRNA.

7. The method of claim 5, wherein the acylimidazole is an a-phenyl substituted imidazole, optionally wherein the acyl group is N,N-dimethyl-phenylglycine.

8. The method of claim 5, wherein a substantially pure stereoisomer of the acylimidazole is used.

9. The method of claim 5, wherein selective acylation comprises:

hybridizing the mRNA to complementary DNA(s) specific for sequences other than the poly-A tail prior to contacting the mRNA with an acylimidazole.

10. The method of claim 1, wherein the RNA is single-stranded or double-stranded, optionally at least 12 nt in length, or greater than 2 kb in length.

11. The method of claim 1, wherein at least 30% of the ribose 2'-OH groups are acylated after step (a).

12. The method of claim 5, wherein at least 30% of the ribose 2'-OH groups in the poly-A tail are acylated after step (a).

13. The method of claim 1, wherein at least 90% of the ribose 2'-OH groups are acylated after step (a).

14. The method of claim 1, further comprising (b) reversing the acylation with a water soluble organocatalyst in aqueous solution at neutral pH.

15. The method of claim 14, wherein the organocatalyst is a strong nucleophile and weak base.

16. The method of claim 15, wherein the organocatalyst is N,N-dimethylglycinate or DABCO (1,4-diazabicyclo [2.2.2]octane).

17. The method of claim 14, wherein step (b) is performed at a pH of from 4 to 5.

18. The method of claim 14, wherein step (b) is performed in an aqueous solution buffered with Tris.

19. The method of claim 14, wherein following step (b) less than about 75% of the RNA is acylated.

20. The method of claim 1, wherein the acylation is spontaneously reversed in a cell environment.

* * * * *